US006852704B1

(12) United States Patent
Levy et al.

(10) Patent No.: US 6,852,704 B1
(45) Date of Patent: Feb. 8, 2005

(54) REVERSE GENE THERAPY

(75) Inventors: Robert J. Levy, Merion Station, PA (US); Scott Baldwin, West Chester, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 263 days.

(21) Appl. No.: 09/487,851

(22) Filed: Jan. 19, 2000

Related U.S. Application Data

(60) Provisional application No. 60/116,539, filed on Jan. 19, 1999.

(51) Int. Cl.$^7$ .................. A61K 48/00; C12P 21/06; C12N 15/74; A01N 63/00; C07H 21/04
(52) U.S. Cl. .................. 514/44; 435/69.1; 435/320.1; 435/325; 435/455; 424/93.2; 424/93.6; 536/23.5
(58) Field of Search ................ 435/320.1, 325, 435/69.1, 455; 424/93.6, 93.2; 536/23.5; 514/44

(56) References Cited

U.S. PATENT DOCUMENTS

| | | |
|---|---|---|
| 4,160,452 A | 7/1979 | Theeuwes |
| 4,256,108 A | 3/1981 | Theeuwes |
| 4,265,874 A | 5/1981 | Bonsen et al. |
| 5,034,506 A | 7/1991 | Summerton et al. |
| 6,207,383 B1 * | 3/2001 | Keating et al. ............. 435/6 |

OTHER PUBLICATIONS

Alton et al. Cationic lipid–mediated CFTR gene transfer to the lungs and nose of patients with cystic fibrosis: a double–blind placebo–controlled trial pp. 947–654 vol 353, 1999.*
Boucher et al. J Clin Invest 1999 Feb.; 103:441–5.*
Okuyama T et al. Gene Ther 1998 Aug.; 8:1047–53.*
Vinyals et al. Gene Ther 1999 Jan.; 6:22–33.*
Bradley et al, J Clin Invest 1999 Mar.; 102;889–96.*
Mazhari, Cir Res 2002:90:842–3.*
Anderson et al., 1995, J. Biomed. Mater. Res. 29:1473–1475.
Anderson et al., 1995, Tissue Eng. 1:323–326.
Antman, 1996, Am. J. Cardiol. 78:67–72.
Arenal et al., 1999, Circulation 99:2771–2778.
Bello et al., 1985, J. Biomol. Struct. Dyn. 2:899–913.
Biben et al., 1996, Develop. Biol. 173:200–212.
Brauner et al., 1997, J. Thorac Cardiovasc Surg 114:923–933.
Buchanan et al., 1993, J. Cardiovasc. Pharmacol. 33:10–14.
Chen et al., 1995, Human Gene Therapy 6:917–926.
Chiquet et al., 1996, Biochem. Cell Biol. 74:737–744.
Chubet et al., 1996, Biotechniques 20:136–141.
Cochrane et al., 1996, Drug Ther. Bull. 34:41–45.
Copertino et al., 1997, Proc. Natl. Acad. Sci. USA 94:1846–1851.
Cosio et al., 1996, Pacing Clin. Electrophysiol. 19:965–975.
Cosio et al., 1993, Lancet 341:1189–1193.
Cosio et al., 1996, Arch. Mal. Coeur Vaiss. 1:75–81.
Couffinhal et al., 1997, Hum. Gene Ther. 8: 929–934.
Cox et al., 1993, Ann. Thorac. Surg. 56:814–823.
Cox et al., 1995, J. Thorac. Cardiovasc. Surg. 110:485–495.
Desai et al., 1996, Pharm. Res. 13:1838–1845.
Desai et al., 1997, Pharm. Res. 14:1568–1573.
Fei et al., 1997, Circ. Res. 80:242–252.
Field, Science 239:1029–1033.
Frame, 1996, Cardiol. Clin. 14:471–481.
Franz et al., 1997, Cardiovascular Research 35:560–566.
Froissart et al., 1998, Clin. Gen. 53:362–368.
Gibson et al., 1995, In: *Molecular Interventions and Local Drug Delivery in Cardiovascular Disease*, Edelman, Ed., W.B. Saunders Co., Ltd., London, UK, pp. 327–352.
Gottsauner–Wolf et al., 1997, Am. Heart J. 133:329–334.
Guzman et al., 1996, Circulation 94:1441–1448.
Hammond et al., 1997, Analyt. Chem. 69:1192–1196.
Huang et al., 1995, Nature 378:292–295.
Humphrey et al., 1997, Adv. Drug Delivery Rev. 24: 87–108.
Hunter et al., 1995, J. Biol. Chem. 270:173–178.
Jain et al., 1991, Anal. Biochem. 199:119–124.
Kaab et al., 1998, Circulation 98:1383–1393.
Kaplan et al., 1998, Biochem. Pharmacol. 55:373–382.
Kim et al., 1998, J. Clin. Invest. 101:1821–1826.
King et al., 1997, J. Biol. Chem. 272:28518–28522.
Labhasetwar et al., 1994, J. Cardiovasc. Pharm. 24:826–840.
Labhasetwar et al., 1995, Clin. Pharmacokinet. 29:1–5.
Labhasetwar et al., 1995, Proc. Natl. Acad. Sci. USA 92:2612–2616.
Labhasetwar et al., 1997, Adv. Drug Del. Rev. 24:109–120.
Labhasetwar et al., 1997, Adv. Drug. Del. Rev. 24:63–85.
Labhasetwar et al., 1998, J. Cardiovasc. Pharmacol. 31:449–455.
Lasic (1997, In: *Gene Delivery*, Lipsows, Ed., CRC Press, Boca Raton, Florida, pp. 33–37 and 56–61.
Levy et al., 1995, J. Controlled Release 36:137–147.
Levy et al., 1996, Drug Delivery 3:137–142.
Martin et al., 1995, Nature 375:691–694.
Martinez–Fong et al., 1994, Hepatology 20:1602–1608.
Mason et al., 1998, Gene Therapy 5:1098–1104.
McDonald et al., 1997, Nature 388:289–292.
Milano et al., 1994, Proc. Natl. Acad. Sci. USA 91: 10109–10113.

(List continued on next page.)

*Primary Examiner*—Janice Li
(74) *Attorney, Agent, or Firm*—Dann, Dorfman, Herrell and Skillman

(57) ABSTRACT

The invention relates to compositions and methods for reverse gene therapy, wherein a gene therapy vector encoding a gene product (e.g. a protein) which is usually only expressed in cells of an abnormal tissue is delivered to a cell of an animal afflicted with a disease or disorder to alleviate the disease or disorder. In one embodiment, a plasmid vector encoding HERG (A561V) protein is delivered to a cell of an animal afflicted with re-entrant atrial flutter-mediated cardiac arrhythmia.

13 Claims, 10 Drawing Sheets

OTHER PUBLICATIONS

Miyamoto et al., 1998, J. Cell. Physiol. 177:58–67.
Nakao et al., 1998, Am. J. Pathol. 152:1237–1245.
Natale et al., 1996, Am. J. Cardiol. 78:1431–1433.
Nielsen et al., 1991, Science 254: 1497.
Nishina et al., 1997, Nature 385:350–353.
Priori et al., 1997, PACE 29:2052–2057.
Radler et al., 1997, Science 275:810–814.
Ranger et al., 1998, Nature 392:186–190.
Rauch et al., 1998, Am. J. Med. Gen. 78:322–331.
Robbins, 1997, Trends Cardiovasc. Med. 7:185–191.
Robbins and Ghivizzani, 1998, Pharmacol. Ther. 80:35–47.
Roden et al., 1996, Annu. Rev. Med. 47:135–48.
Rodefeld et al., 1996, J. Thorac. Cardiovasc. Surg. 112:898–907.
Sanguinetti et al., 1995, Cell 81:299–307.
Sanguinetti et al., 1996, Nature 384:80–83.
Sanguinetti et al., 1996, Proc. Natl. Acad. Sci. USA. 93:2208–2212.
Schneider et al., 1998, FEBS Letters 429:269–273.
Schwendeman et al., 1995, Pharm. Res. 12:790–795.
Shelness et al., 1994, J. Biol. Chem. 269:9310–9318.
Sintov et al., 1997, Int. J. Pharm. 146:55–62.
Solway et al., 1995, J. Biol. Chem. 270:13460–13469.
Song et al., 1997, J. Controlled Release 45:177–192.
Subramanian et al., 1995, Cell Growth Differ. 6: 131–137.
Villa et al., 1995, Circ. Res. 76:505–513.
Waldo, 1994, Clin. Cardiol. 17:1121–1126, 1994.
Wang et al., 1997, Current Op. Cardio. 12:310–320.
Wells et al., 1979, Circulation 60:665–673.
Wolfert et al., 1996, Gene Therapy 3:269–273.
Wolfert et al., 1996, Human Gene Therapy 7:2123–33.
Wood et al., 1995, In: *Molecular Interventions and Local Drug Delivery in Cardiovascular Disease*, Edelman, Ed., W.B. Saunders Co., LTD, London, UK, pp. 399–471.
Zhou et al., 1999, J. of Biol. Chem. 274:31123–31126.

* cited by examiner

REVERSE GENE THERAPY

CROSS-REFERENCE TO RELATED APPLICATIONS

This application is entitled to priority pursuant to 35 U.S.C. §119(e) to U.S. provisional patent application No. 60/116,539, which was filed on Jan. 19, 1999.

STATEMENT REGARDING FEDERALLY SUPPORTED RESEARCH AND DEVELOPMENT

This research was supported in part by U.S. Government funds (National Heart, Lung and Blood Institute Grant number HL41663), and the U.S. Government may therefore have certain rights in the invention.

BACKGROUND OF THE INVENTION

Re-entrant atrial flutter is a disease condition which affects many individuals. Electrophysiologic mapping techniques have lead to an enhanced understanding re-entrant atrial arrhythmias, and these advances have led to attempts to develop ablation procedures which destructively block conduction in myocardial regions involved in re-entry (e.g. a band of conductive tissue designated the crista terminalis which is involved in aberrant myocardial conduction associated with atrial flutter; Natale et al., 1996, Am. J. Cardiol. 78:1431–1433; Frame et al., 1996, Pacing Clin. Electrophysiol. 19:965–975; Cosio et al., 1996. Arch. Mal. Coeur Vaiss. 1:75–81; Cox et al., 1995, J. Thorac. Cardiovasc. Surg. 110:485–495, Cox et al., 1993. Ann. Thorac. Surg. 56:814–823; Cox et al., 1996, J. Thorac. Cardiovasc. Surg. 112:898–907; Arenal et al., 1999, Circulation 99:2771–2778).

BRIEF SUMMARY OF THE INVENTION

The invention relates to a method of alleviating a disease or disorder in an affected animal cell. The method comprises locally delivering to the cell a reverse gene therapy vector comprising a promoter operably linked with a nucleic acid encoding a therapeutic gene product which is usually only expressed in cells of an abnormal tissue that is not afflicted with the disease or disorder. Delivery of the reverse gene therapy vector to the affected cell and expression of the gene product therein alleviates the disease or disorder.

In one aspect of this method, the therapeutic gene product is a protein, such as one selected from the group consisting of a defective HERG protein, an apoptosis-inducing protein, transcription factor E2F1, tenascin C, bone morphogenic protein, a protein involved in synthesis of a glycosaminoglycan, a dominant negative mutant receptor protein, transcription factor NF-ATc, a mutant fibroblast growth factor receptor protein, and a degradation resistant collagen protein. Preferably, the protein is a defective HERG protein, such as HERG (A561V) protein.

In another aspect of the method, the reverse gene therapy vector is selected from the group consisting of naked DNA, a plasmid, a condensed nucleic acid, and a virus vector comprising a nucleic acid. The reverse gene therapy vector can, for example, be a virus vector (such as an adenovirus vector, a retrovirus vector, an adeno-associated virus vector, or a herpes virus vector), or a condensed nucleic acid. When a condensed nucleic acid reverse gene therapy vector is used, it can comprise a DNA molecule and a polycationic condensing agent.

In still another aspect of the method, the reverse gene therapy vector is a plasmid.

The polycationic condensing agent used in the method described herein can, for example, be selected from the group consisting of poly-L-lysine and $Ca^{2+}$ ions. The promoter can be any promoter, including a constitutive promoter such as a CMV Atrial fibrillation and atrial flutter are emerging as major clinical and public health problems for a number of reasons. The high incidence of atrial arrhythmias in the increasingly-aged population has resulted in the number of patients afflicted with atrial fibrillation or atrial flutter increasing into the millions (Prystowsky et al., 1996, Circulation 93:1262–1277; Anderson et al., 1996, Am. J. Cardiol. 78:17–21; Camm et al., 1996, Am. J. Cardiol. 78:3–11). In addition, atrial fibrillation and atrial flutter have been noted to occur very commonly following cardiac surgery, especially following coronary artery bypass surgery (Cox, 1993, Ann. Thorac. Surg. 56:405–409; Balaji et al., 1994, Am. J. Cardiol. 73:828–829; Balaji et al., 1994, J. Am. Coll. Cardiol. 23:1209–1215; Gandhi et al., 1996, Ann. Thorac. Surg. 61:1299–1309).

A number of mechanisms have been investigated to explain atrial arrhythmias, and are the basis for the conventional therapeutic approach. Re-entrant phenomena are thought to most often be the basis for atrial flutter (Gandhi et al., 1996, Ann. Thorac. Surg. 61:1666–1678; Frame et al., 1986, Circ. Res. 58:495–511; Frame et al., 1987, Circulation 5:1155–1175; Boyden et al., 1989, Circulation 79:406–416; Cosio et al., 1993, Lancet 341:1189–1193). Medications that slow atrial conduction or block down conduction through the AV-node have been useful for treatment of atrial arrhythmias (Waldo, 1994, Clin. Cardiol. 17:1121–1126, 1994; Wells et al., 1979. Circulation 60:665–673; Antman, 1996, Am. J. Cardiol. 78:67–72; Cochrane et al., 1996, Drug Ther. Bull. 34:41–45; Roden et al., 1996, Annu. Rev. Med. 47:135–48). Atrial fibrillation is believed often to result from a coalescence of multiple wavelets of impulse conduction (Moe, 1962, Arch. Int. Pharmacodyn. 1–2:183–188; Waldo, 1990. Circulation 81:1142–1143), and recent investigations have suggested that conditioned fibrillating atrium begets further atrial fibrillation (Salmon et al., 1985, Circulation 72(Suppl III):111–250; Morillo et al., 1995. Circulation 91:1588–1595; Wijffels et al., 1995. Circulation 92:1954–1968).

Gene Therapy

Gene therapy is generally understood to refer to techniques designed to deliver nucleic acids, including antisense DNA and RNA, ribozymes, viral genome fragments and functionally active therapeutic genes into targeted cells (Culver, 1994. *Gene Therapy: A Handbook for Physicians*. Mary Ann Liebert, Inc., New York, N.Y.). Such nucleic acids can themselves be therapeutic, as for example antisense DNAs that inhibit mRNA translation, or they can encode, for example, therapeutic proteins that promote, inhibit, augment, or replace cellular functions.

Virus vectors are among the most efficient gene therapy vectors which have been demonstrated. However, virus vectors sometimes elicit an immune response in the gene therapy host, which can inhibit the therapeutic benefit provided by the vector. Furthermore, use of retrovirus vectors can result in integration of the nucleic acid of the vector into the genome of the host, potentially causing harmful mutations. 'Naked' nucleic acid vectors, such as linear DNA vectors and plasmids, do not generally induce an immune response or integrate into the host genome, but are taken up and expressed by host cells less effectively than virus vectors.

Among the shortcomings of current gene therapy strategies, including both ex vivo and in vivo gene therapy methods, is a dearth of appropriate nucleic acids for delivery to diseased or otherwise abnormal cells. Gene therapy methods have typically involved delivery of either a nucleic acid which is or which encodes a normal (i.e. wild type) component of a cell of the type to which the nucleic acid is delivered, an antisense oligonucleotide which inhibits or prevents transcription or translation of a nucleic acid in the diseased or abnormal cells, or a ribozyme which specifically cleaves a nucleic acid in diseased or abnormal cells. Although these nucleic acids can be effective in certain instances, a serious need remains for additional nucleic acids which, when delivered to diseased or abnormal cells, alleviate, prevent, or reverse the disease or abnormality. Furthermore, a gene therapy method which exerts its physiological effects by a mechanism which differs from the mechanism employed in previous gene therapy methods would be beneficial.

The present invention relieves these needs by providing compositions and methods for gene therapy which differ from the gene therapy compositions and methods of the prior art. promoter or a tissue-specific promoter such as a cardiac tissue-specific promoter (e.g. the ANF promoter or the α-MyHC promoter).

The reverse gene therapy vector used in the method described herein can further comprise a pharmacological agent-sensitive enhancer, such as a phorbol ester-sensitive enhancer. The reverse gene therapy vector can also, or alternatively, further comprise a Cre-recombinase-sensitive site.

According to the method of the invention, the reverse gene therapy vector can be delivered to the cell in a sustained-release manner. Such delivery methods can, for example, comprise delivering the reverse gene therapy vector to the cell in a form selected from a particle comprising the vector, a microparticle comprising the vector, a nanoparticle comprising the vector, an implantable device having a surface coated with a matrix comprising the vector, or a bulk material comprising the vector. The implantable device can, for example, comprise an electrode located in close proximity to a myocardial tissue of the animal, such as right atrial myocardium.

In one embodiment of the method described herein, the cell is located outside the body of the animal. The cell can, for example, be a cultured cell, such as a cultured cell which is subsequently returned to the body of the animal from which the cell was obtained or is subsequently returned to the body of a second animal other than the animal from which the cell was obtained.

In another embodiment of the method described herein, the cell is located inside the body of the animal. For example, the cell can be located in a cardiac tissue of the animal, such as a myocardial cell (e.g. a right atrial myocardium cell or a cell of the crista terminalis). The animal can be one which is afflicted with re-entry atrial flutter, in which event the therapeutic gene product is preferably a defective HERG protein, such as HERG (A561V) protein. Also preferably, the protein is operably linked with a cardiac tissue-specific promoter, such as one selected from the group consisting of the ANF promoter and the α-MyHC promoter.

The invention also relates to a reverse gene therapy vector for alleviating a disease or disorder in an affected cell. The vector comprises a promoter operably linked with a nucleic acid encoding a therapeutic gene product which is normally only expressed in cells of an abnormal tissue that is not afflicted with the disease or disorder. Delivery of the vector to the affected cell and expression of the gene product therein alleviates the disease or disorder.

In one aspect, the therapeutic gene product is a protein, such as one selected from the group consisting of a defective HERG protein, an apoptosis-inducing protein, transcription factor E2F1, tenascin C, bone morphogenic protein, a protein involved in synthesis of a glycosaminoglycan, a dominant negative mutant receptor protein, transcription factor NF-ATc, and a degradation resistant collagen protein. When the protein is a defective HERG protein, it is preferably HERG (A561V) protein.

In another aspect of the reverse gene therapy vector, the vector is selected from the group consisting of naked DNA, a plasmid, a condensed nucleic acid, and a virus vector comprising a nucleic acid. In one embodiment, the vector is a virus vector such as an adenovirus vector. In another embodiment, the vector is a condensed nucleic acid, such as one comprising a DNA molecule and a polycationic condensing agent. In still another embodiment, the gene therapy vector is a plasmid.

The polycationic condensing agent of the reverse gene therapy vector can, for example, be selected from the group consisting of poly-L-lysine and $Ca^{2+}$ ions.

The promoter used in the reverse gene therapy vector can be substantially any promoter, including a constitutive promoter such as a CMV promoter or a tissue-specific promoter such as a cardiac tissue-specific promoter (e.g. the ANF promoter, the α-MyHC promoter, and the wild type HERG promoter).

The reverse gene therapy vector can further comprise a pharmacological agent-sensitive enhancer, such as a phorbol ester-sensitive enhancer. The reverse gene therapy vector can also, or alternatively, comprising a Cre-recombinase-sensitive site.

The invention also includes a particle, a microparticle, or a nanoparticle comprising the reverse gene therapy vector.

The invention further includes an implantable device comprising the reverse gene therapy vector, such as one having a surface coated with a matrix comprising the reverse gene therapy vector.

BRIEF DESCRIPTION OF THE DRAWINGS

FIG. 4, comprising FIGS. 4A and 4B are graphs which indicate the amount of DNA released from these nanoparticles when they were incubated in vitro in TE buffer which did or did not contain SDS. FIG. 4C is a bar graph which indicates luciferase activity in type 293 cells transformed using DNA-containing PLGA copolymer nanoparticles.

DETAILED DESCRIPTION

Figure 1:
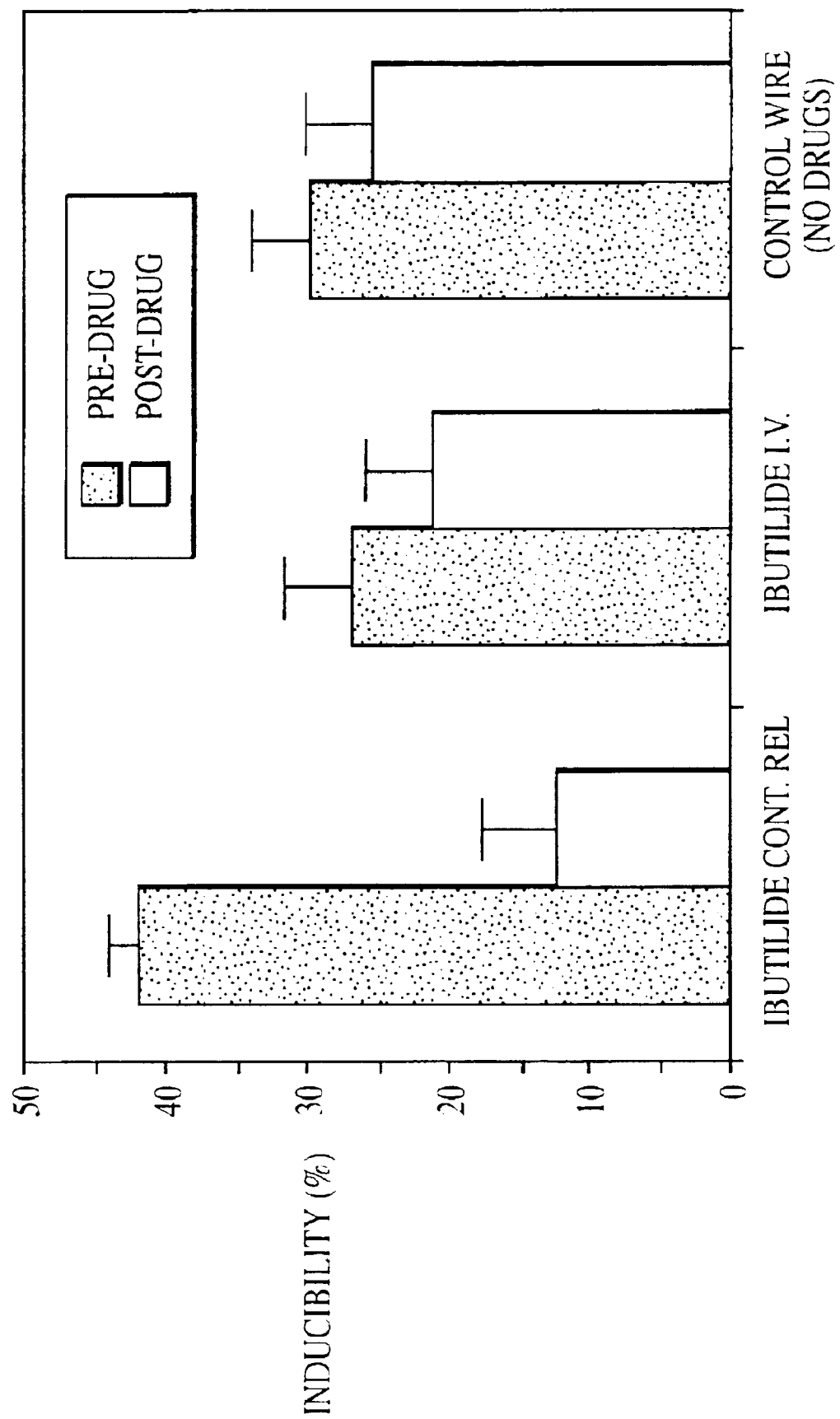
FIG. 1 is a bar graph which indicates inducibility of atrial flutter in dogs implanted with epicardial pacing electrodes, as described herein.

The invention relates to a new method of gene therapy herein designated 'reverse' gene therapy. Traditional gene therapy methods involve using a gene vector to deliver a wild type or engineered gene or a promoter operably linked with a nucleic acid encoding a wild type or engineered protein or a wild type or engineered RNA molecule to an cell of an animal afflicted with a disease or disorder.

'Reverse' gene therapy, as described herein, refers to localized delivery of a gene therapy vector which comprises a nucleic acid to an affected cell of an animal afflicted with a disease or disorder. The nucleic acid encodes a therapeutic gene product which is usually only expressed in cells of an abnormal tissue which is not afflicted with the same disease or disorder. Such abnormal tissues include, for example, tissues afflicted with a different disease or disorder than the one being alleviated by reverse gene therapy. Because the therapeutic gene product is expressed in an abnormal tissue, expression of the therapeutic gene product in tissues other than the tissue afflicted with the disease or disorder being alleviated is generally considered by others to be undesirable (despite the 'therapeutic' designation attached to such gene products in the present disclosure). Hence, it is necessary to minimize or prevent expression of the therapeutic gene product in normal tissues by delivering the gene therapy vector in a localized fashion, and preferably by expressing the therapeutic gene product in a tissue-specific manner. Also preferably, the gene therapy vector is administered in a sustained-release fashion in order to maximize and extend expression of the therapeutic gene product in the tissue afflicted with the disease or disorder being treated. The word "reverse" in reverse gene therapy emphasizes a nucleic acid construct which would be harmful if expressed in one physiological setting is delivered to a diseased physiological site in order to achieve the reverse (i.e. a beneficial) effect in a different setting.

The reverse gene therapy method is a method of alleviating a disease or disorder in an affected animal cell. This method comprises locally delivering to the cell a gene therapy vector. The gene therapy vector comprises a promoter operably linked with a nucleic acid encoding a therapeutic gene product which is usually only expressed in cells of an abnormal tissue that is not afflicted with the disease or disorder, such as cells of a tissue afflicted with a different disease or disorder. Delivery of the gene therapy vector to the affected cell and expression of the therapeutic gene product therein alleviates the disease or disorder in the cell. By alleviating the disease or disorder in individual affected cells of an animal afflicted with a disease or disorder, the symptoms of the disease or disorder are alleviated. In contrast with alleviation of symptoms effected by administration of non-nucleic acid-containing pharmaceutical agents, administration of the gene therapy vector described herein results in a longer period of relief from the symptoms. If the gene therapy vector comprises a virus vector which is capable of integrating its nucleic acid into the genome of the cell or into the genome of an organelle within the cell, very long term relief can be effected, possibly enduring for the length of the animal's life.

Preferred compositions and methods for reverse gene therapy which are described herein include compositions and methods for delivering a gene therapy vector to cardiac tissue in an animal afflicted with a cardiac disease or disorder such as cardiac arrhythmias. Localized delivery of pharmaceutical agents to cardiac tissue has been described by others (e.g. Labhasetwar et al., 1998, J. Cardiovasc. Pharmacol. 31:449–455; Labhasetwar et al., 1997, Adv. Drug Del. Rev. 24:109–120; Labhasetwar et al., 1997, Adv. Drug. Del. Rev. 24:63–85; Sintov et al., 1997, Int. J. Pharm. 146:55–62; Gottsauner-Wolf et al., 1997. Am. Heart J. 133:329–334; Humphrey et al., 1997, Adv. Drug Delivery Rev. 24: 87–108; Desai et al., 1997, Pharm. Res. 14:1568–1573; Song et al., 1997, J. Controlled Release 45:177–192).

Localized delivery of an agent such as a gene therapy vector advantageously delivers the agent only or primarily to a particular site, minimizes the amount of agent which needs to be delivered (i.e. by minimizing delivery to undesired sites), and minimizes undesirable effects caused by delivery of the agent systemically or to tissues located at a distance from the particular site. By way of example, enhanced efficacy of various anti-arrhythmic agents has been demonstrated when the agents were locally delivered, relative to the efficacy of the same agents delivered systemically (Labhasetwar et al., 1997, Adv. Drug Del. Rev. 24:109–120; Labhasetwar et al., 1997, Adv. Drug. Del. Rev. 24:63–85; Sintov et al., 1997, Int. J. Pharm. 146:55–62; Gottsauner-Wolf et al., 1997, Am. Heart J. 133:329–334; Humphrey et al., 1997, Adv. Drug Delivery Rev. 24:87–108; Desai et al., 1997, Pharm. Res. 14:1568–1573; Song et al., 1997, J. Controlled Release 45:177–192). Reduction of ventricular defibrillation thresholds has also been associated with local cardiac drug delivery (Song et al., 1997. J. Controlled Release 45:177–192).

A drawback of sustained-release drug delivery of a conventional pharmaceutical agent is the need to continuously resupply drug to the drug reservoir because of depletion or turnover of the drug. Sustained-release delivery of many anti-arrhythmics is further hindered by the relatively non-specific effect of such agents and by the fact that local delivery of such agents fails to change the nature of the underlying pro-arrhythmic myocardium. Thus, when delivery of anti-arrhythmic agent ceases, the myocardium remains pro-arrhythmic.

Traditional gene therapy methods have not been useful for treating pro-arrhythmic myocardium because of several factors. First, no reasonable candidate genes have been proposed for delivery to pro-arrhythmic myocardium. Second, delivery systems for localizing gene vector delivery to specific arrhythmogenic circuits within the heart have not been previously described. Third, numerous gene vectors suggested for gene therapy have exhibited complications relating to, among other things, systemic immunogenicity and toxicity. The present invention overcomes these shortcomings. As described herein, reverse gene therapy can be used to appropriately alter myocardial sites involved in mechanistic events leading to re-entrant arrhythmias because use of pathologic mutants of ion channel proteins defeats tachyarrhythmic conduction circuits and achieves, in essence, a "biotech ablation" of such arrhythmias. Perhaps because these mutant proteins are usually only expressed in cells of an abnormal tissue, their use to treat alleviate arrhythmias and other cardiac disease and disorders has not been contemplated by others.

The identity of the therapeutic gene product is not critical. This gene product need only be one which will alleviate the disease or disorder in the affected cells or tissues. When the disease or disorder is re-entry atrial flutter, the gene product can be any gene product that reduces myocardial conductivity in atrial tissue. Examples of such gene products include mutated ion channel proteins and their subunits. These proteins and normally-disease/disorder-associated mutant forms thereof, are described, for example in McDonald et al. (1997, Nature 388:289–292). Expression of such proteins/subunits is normally associated with a disease or disorder. However, when these proteins/subunits are expressed in atrial tissue in a subject afflicted with re-entry atrial flutter, conductivity of the tissue is reduced, and the atrial flutter is alleviated. An example of an ion channel protein is HERG.

HERG refers to the human ether agogo gene, which encodes a potassium channel rectifier protein that modulates myocardial $K^+$ re-entrant current. HERG (A561V) refers to a point mutation (resulting in an alanine-to-valine substitution) in this protein, which is responsible for one of the forms of the Long QT Syndrome, a hereditary disorder associated with episodes of ventricular arrhythmias and a risk of sudden death (Labhasetwar et al., 1995. Proc. Natl. Acad. Sci. USA 92:2612–2616; Schwendeman et al., 1995, Pharm. Res. 12:790–795; Labhasetwar et al., 1995, Clin. Pharmacokinet. 29:1–5: Levy et al., 1995, J. Controlled Release 36:137–147; Gibson et al., 1995, In: *Molecular Interventions and Local Drug Delivery in Cardiovascular Disease*, Edelman, Ed., W. B. Saunders Co., Ltd., London, UK, pp. 327–352; Wood et al., 1995. In: *Molecular Interventions and Local Drug Delivery in Cardiovascular Disease*, Edelman. Ed., W. B. Saunders Co., Ltd., London, UK, pp. 399–471). The HERG gene resides on chromosome 7 (q35–36), and has a length of about 3.2 kilobases, cDNA encoding HERG (A561V) protein has been incorporated into a plasmid vector by others, and this plasmid was used to define the mechanism of its role in the Long QT Syndrome (Wood et al., 1995, In: *Molecular Interventions and Local Drug, Delivery in Cardiovascular Disease*, Edelman, Ed., W. B. Saunders Co., LTD, London, UK, pp. 399–471). Expression of HERG (A561V) in *Xenopus oocytes* depressed the tail current response to various test pulses of voltage amplitudes, which indicated that HERG (A561V) becomes associated with the cell membrane following introduction of exogenous genetic material (Sanguinetti et al., 1996, Proc. Natl. Acad. Sci. USA. 93:2208).

The HERG (A561V) gene encodes a defective potassium channel rectifier. Defective HERG (A561V) protein interacts with the wild type HERG potassium channel rectifier in a dominant negative manner, thereby inhibiting $K^-$ current through the HERG membrane protein. Expression of the defective HERG (A561V) protein in the cell membrane of cardiac myocytes results in prolonged myocardial conduction. Ibutilide, a short acting Class III anti-arrhythmic agent, also blocks cardiac potassium channel rectifier current and delays myocardial conduction. Ibutilide has been administered to patients to prevent re-entrant atrial flutter. Because both ibutilide and defective HERG (A561V) protein inhibit $K^-$ current through the HERG membrane protein, administration of defective HERG (A561V) protein to a patient afflicted with re-entrant atrial flutter using a reverse gene therapy method as described herein will relieve this condition. Prior to ethical use of this reverse gene therapy method on human patients, the method is tested using dogs. Dogs are utilized in these studies, because of the extensive prior work by the inventors and many others on dog models of cardiac arrhythmias and, in particular, atrial flutter (e.g. Kirshenbaum et al., 1996, Develop. Biol. 179:402–411; Cox et al., 1995, J. Thorac. Cardiovasc. Surg. 110:485–495). Dog myocardium is thus an art-recognized model of human myocardium, at least for the purposes of assessing the effectiveness of alleviating re-entrant atrial flutter.

Although the compositions and methods described herein focus on use of HERG (A561V), one or more of the other point mutations which have been described in the human ether agogo gene can be similarly used (e.g. Labhasetwar et al., 1995, Proc. Natl. Acad. Sci. USA 92:2612–2616; Schwendeman et al., 1995, Pharm. Res. 12:790–795; Labhasetwar et al., 1995, Clin. Pharmacokinet. 29:1–5; Levy et al., 1995, J. Controlled Release 36:137–147; Gibson et al., 1995, In: *Molecular Interventions and Local Drug Delivery in Cardiovascular Disease*, Edelman, Ed., W. B. Saunders Co., Ltd., London, UK, pp. 327–352). Alternatively, re-entrant circuit block can elicited by localized delivery and expression of the transcription factor, E2F1, which causes apoptosis in mature myocytes (Levy 1995, In: *Molecular Interventions and Local Drug Delivery in Cardiovascular Disease*, Edelman, Ed., London, UK: W. B. Saunders Co., Ltd.; Anderson et al., 1995, J. Biomed. Mater. Res. 29:1473–1475), thereby creating a devitalized region (by means of gene-induced apoptosis) within a re-entry loop.

Another example of a mutant HERG gene that is normally associated with an aberrant physiological condition (i.e. a disease or disorder) is the gene encoding the beta subunit of HERG. This gene encodes a protein that is designated MIRP (McDonald et al., 1997, Nature 388:289–292). MIRP mutants normally interfere with the physiological function of HERG, resulting in a disease condition. However, providing a MIRP mutant to atrial myocardium in a subject afflicted with re-entry atrial flutter decreases the conductivity of the atrial tissue, thereby alleviating the disorder.

The therapeutic gene product described herein is not limited to mutant ion channel proteins. The therapeutic gene product can be any gene product expression of which is associated with a first disease or disorder in an animal tissue, but which alleviates a different disease or disorder when it is expressed in an animal afflicted with a different disease or disorder. For example, many diseases and disorders can be alleviated by ablating particular cells or tissues. Thus, using the methods described herein, expression in those cells or tissues of a gene product that ablates those cells or tissues in a different disease or disorder leads to death of the cells/tissues. By way of example, a mutant fibroblast growth factor receptor protein is associated with induced apoptosis of smooth muscle cells in animal cells (Miyamoto et al., 1998, J. Cell. Physiol. 177:58–67). To continue the example involving re-entry atrial flutter, expression of this mutant receptor protein in atrial myocardial cells of an animal afflicted with re-entry atrial flutter induces apoptosis in those cells, ablating the conductive loop associated with the disorder. Thus, providing this mutant protein to these cells using the methods described herein alleviates the disorder.

Localization of delivery of an agent encoded by a nucleic acid can be enhanced by use of a tissue-specific or physiologically responsible promoter operably linked with the nucleic acid encoding the agent. Numerous tissue-specific and physiologically responsible promoters have been described. For example, tissue specific promoters and physiologically responsible promoters include the sm22alpha promoter, which specifically promotes expression of genes in arterial smooth muscle cells (Solway et al., 1995, J. Biol.

Chem. 270:13460–13469) and the tenascin-C promoter, which specifically promotes expression of genes in proliferating cells in response to the presence of matrix metalloproteinase-modified collagens (Chiquet et al., 1996, Biochem. Cell Biol. 74:737–744: Copertino et al., 1997, Proc. Natl. Acad. Sci. USA 94:1846–1851).

A physiologic responsive promoter is a nucleotide sequence which regulates downstream DNA expression in response to a change in the regional physiology such as an alteration in the extracellular matrix (i.e. collagen breakdown or denaturation), an increase in regional temperature to the febrile range, or a response to a change in blood pressure or blood flow.

In the reverse gene therapy compositions and methods described herein for treatment of cardiac arrhythmias, the promoter is preferably a cardiac tissue-specific promoter, such as the α-myosin heavy chain promoter (α-MyHC; Anderson et al., 1995, Tissue Eng. 1:323–326; Villa et al., 1995. Circ. Res. 76:505–513) or the atrial natriuretic factor promoter (ANF; Guzman et al., 1996. Circulation 94:1441–1448). Of course, non-tissue-specific promoters (e.g. the wild type HERG promoter) and constitutive promoters (e.g. a cytomegalovirus {CMV} promoter) can be used in the gene therapy vector described herein.

Localized expression of a therapeutic gene product can be enhanced in a reverse gene therapy method by delivering a gene therapy vector having a nucleic acid which comprises a pharmacological agent-sensitive enhancer element in addition to the portion of the nucleic acid encoding the therapeutic gene product. A variety of such pharmacological agent-sensitive enhancer agents have been described, such as those which enhance gene expression in response to administration of a phorbol ester to a cell which comprises a nucleic acid having such an enhancer element (Desai et al., 1996, Pharm. Res. 13:1838–1845; Levy et al., 1996, Drug Delivery 3:137–142; Song et al., 1997, J. Controlled Release 43:197–212). Localized enhancement of expression of the therapeutic gene product can be effected by localized delivery of the gene therapy vector coupled with systemic delivery of the pharmacological agent corresponding to the enhancer element, by systemic delivery nf the gene therapy vector coupled with localized delivery of the pharmacological agent corresponding to the enhancer element, or, preferably, by localized delivery of both the gene therapy vector and the pharmacological agent corresponding to the enhancer element.

Expression of a gene product encoded by the gene therapy vector described herein can be rendered terminable by incorporating a Cre-recombinase sensitive site in the nucleic acid of the gene therapy vector, as described (Hammond et al., 1997, Analyt. Chem. 69:1192–1196). Expression of the gene product in a cell transformed using the gene therapy vector is terminated by delivering a second vector to the cell, wherein the second vector encodes Cre-recombinase.

In an alternative embodiment of the invention, the gene therapy vector encodes a protein which, when expressed in a cell, induces apoptosis of the cell. Such proteins include, for example the transcription factor E2F1 and transcription factors normally encoded by viruses (Levy, 1995, In: *Molecular Interventions and Local Drug Delivery in Cardiovascular Disease*, Edelman. Ed., London, UK: W. B. Saunders Co., Ltd.; Anderson et al., 1995. J. Biomed. Mater. Res. 29:1473–1475; Martin et al., 1995. Nature 375:691–694). Another example of such a protein is the mutant fibroblast growth factor receptor protein described above.

Other specific embodiments of the invention include the following:

Delivery of a gene therapy vector encoding a mutant tenascin C protein associated with a disease state to cardiac or coronary artery tissue, in order to limit or prevent progression or development of cardiac valve obstruction or coronary artery obstruction. Tenascin C normally organizes progressive deposition of extracellular matrix. In certain disease states, expression of mutant tenascin C proteins lead to repression of extracellular matrix production (Nakao et al., 1998, Am. J. Pathol. 152:1237–1245).

Delivery of a gene therapy vector encoding a bone morphogenic protein (BMP) under the transcriptional control of a mutant BMP promoter associated with a disease state to a bone fracture site or to a bone site at risk of fracture (e.g. bone non-union sites, sites at which reconstructive surgery has been performed, and cranio-facial sites). In certain disease states, mutant BMP promoters lead to overexpression of BMP (Kaplan et al., 1998, Biochem. Pharmacol. 55:373–382).

Delivery of a gene therapy vector comprising at least a portion of a mutant gene associated with one or more mucopolysaccharidoses to a glycosaminoglycan- (GAG-) deficient site or to a biomechanically compromised site (e.g. a joint, tendon, or heart valve) in the body of an animal. As is known, various mutant genes associated with one or more mucopolysaccharidoses result in overexpression of GAG in the affected tissue (Froissart et al., 1998, Clin. Gen. 53:362–368).

Delivery of a gene therapy vector encoding a mutant gene, expression of which mutant gene is associated with apoptosis in a disease state, to cells or tissue which contributes to a different disease state (e.g. delivery of an apoptosis-inducing gene to myocardium cells which form all or part of conduction pathway associated with arrhythmia). Numerous mutant genes are known, expression of which mutant gene is associated with apoptosis in a disease state (e.g. Nishina et al., 1997, Nature 385:350–353).

Delivery of a gene therapy vector encoding a mutant gene encoding a dominant negative mutant gene product associated with a disease state to cells or tissue which is affected by a disease state associated with the normal (i.e. non-mutant) form of the gene product. By way of example, dominant negative mutant variants of numerous cell-surface receptors are known, such as dominant negative mutants wherein one or more inoperative receptor subunits ablate the activity of a multi-subunit receptor (e.g. Kim et al., 1 998, J. Clin. Invest. 101:1821–1826).

Delivery of a gene therapy vector encoding therapeutic gene product which is usually only expressed in cells of an abnormal tissue to facilitate implantation of engineered tissue (e.g. cultured organ tissue) into an animal. For example, a vector comprising a disease-associated gene could be used to favorably modify a tissue prior to implantation of the tissue. By way of specific example, a gene that normally encodes a product which, when expressed, induces a skeletal defect (e.g. a gene described by Kaplan et al., 1998, Biochem. Pharmacol. 55:373–382) can be delivered to a tissue-engineered heart valve prior to implantation of the valve in a patient in order to prevent the valve from calcifying.

Delivery of a gene therapy vector encoding an uncontrollable mutant of the transcription factor NF-ATc to cardiac tissue of a post-natal individual to facilitate development of a cardiac valve. The role of transcription factor NF-ATc in abnormal cardiac valve formation has been described (Ranger et al., 1998, Nature 392:186–190).

Delivery of a gene therapy vector comprising a pressure- or flow-unresponsive mutant tenascin C gene (or cDNA) to cardiac tissue to retard or prevent cardiac valve obstruction. Such mutant tenascin C genes have been described (e.g. Huang et al., 1995, Nature 378:292–295).

Delivery of a gene therapy vector encoding a degradation resistant protein normally associated with a disease state to cells or tissue affected by a different disease state associated with the corresponding normal (i.e. degradation sensitive) form of the protein. For example, a gene therapy vector encoding a mutant collagen protein which is resistant to degradation by matrix metalloproteinase (MMP) can be delivered to a cell to block MMP cascade-integrin signaling (King et al., 1997, J. Biol. Chem. 272:28518–28522).

Delivery of a gene therapy vector comprising a gene having a deletion therein, relative to the wild type gene, wherein expression of the gene having the deletion is normally associated with a disease state, but when the gene therapy vector is delivered to cells or tissue affected by a different disease state, expression of the gene having the deletion alleviates or inhibits the different disease state. For example, chromosomal deletions such as the chromosome 22 deletions associated with cardiac defects (e.g. those described by Rauch et al., 1998. Am. J. Med. Gen. 78:322–331) can be used to inhibit heart valve calcification through by delivering vectors comprising antisense constructs corresponding to the deleted regions of chromosome 22. Delivery of such vectors to heart valve tissue suppresses differentiation of potentially calcifying cells in cardiac valves and blood vessels.

The Reverse Gene Therapy Vector

The invention includes a reverse gene therapy vector which is useful for alleviating a disease or disorder in a cell. This reverse gene therapy vector comprises a promoter operably linked with a nucleic acid encoding a therapeutic gene product which is normally only expressed in cells of an abnormal tissue that is not afflicted with the same disease or disorder. Delivery of the vector to the cell alleviates the disease or disorder.

The therapeutic gene product encoded by gene therapy vector described herein can, for example, be a protein, a ribozyme, an antisense RNA molecule, or another molecule which, when expressed in a normal cell, causes the normal cell to exhibit a symptom associated with a disease or disorder but which, when expressed in a cell to which the gene therapy vector is delivered, alleviates a symptom of a disease or disorder which affects the cell. Proteins which can be encoded by the gene therapy vector include defective HERG proteins, HERG (A561V) protein, apoptosis-inducing proteins, and transcription factor E2F1.

The reverse gene therapy vector can be substantially any nucleic acid vector which is now known or hereafter developed. Exemplary vectors include naked DNA vectors, plasmids, condensed nucleic acids, and virus vectors. In a preferred embodiment of the reverse gene therapy vector, the vector is a plasmid, and more preferably comprises both a plasmid and a condensing agent such as poly-L-lysine or $Ca^{2+}$ ions. When the vector is a virus vector, the virus vector is preferably one of an adenovirus vector, a retrovirus vector, an adeno-associated virus vector, and a herpes virus vector.

Plasmid DNA transformation of mammalian cells results in plasmid DNA residing in the nucleus of the transfected cell, wherein the plasmid not incorporated into a chromosome. Transient episomal expression of plasmid DNA generally occurs following transformation (Dowty et al., 1995, Proc. Natl. Acad. Sci. USA 92:4572–4576; Wolff et al., 1996. Hum. Mol. Genet. 1:363–369; Fritz et al., 1996, Hum. Gene Ther. 7:1395–404). Plasmid transformation of cardiac and skeletal striated muscular tissue, either cardiac or skeletal, has been demonstrated following administration of naked DNA to such tissue, and expression of the DNA in the transformed cells has been observed to persist for months (Dowty et al., 1995. Proc. Natl. Acad. Sci. USA 92:4572–4576; Wolff et al., 1996, Hum. Mol. Genet. 1:363–369. Fritz et al., 1996, Hum. Gene Ther. 7:1395–404). Alternatively, a gene therapy vector, such as any of certain virus vectors, can be used, wherein the vector causes the nucleic acid carried thereby to be integrated into the host cell genome.

The gene therapy vector described herein is preferably administered to a cell or tissue of an animal in a sustained-release manner. Numerous methods have been described for effecting sustained release of a nucleic acid vector such as a gene therapy vector, and all known and hereafter-developed methods for achieving sustained release of a nucleic acid vector can be used in accordance with the compositions and methods described herein. The gene therapy vector is preferably DNA in the form of a plasmid, particularly condensed plasmid DNA incorporated into particles, microparticles, nanoparticles, a bulk material, or a coating present at a surface of an implantable device. Preferred nucleic acid vector compositions and methods of using them to administer a vector, such as the gene therapy vector described herein, are described in commonly-assigned U.S. patent applications having application Ser. Nos. 60/116,538; 60/116,405; and Ser. No. 09/234,011, each of which shares a common priority date with the present disclosure, and each of which is incorporated herein by reference.

When the gene therapy vector described herein comprises a gene therapy vector for delivering a therapeutic gene product to a cardiac tissue in order to alleviate a cardiac arrhythmia, the vector is preferably delivered to myocardial tissue in the animal. When the cardiac arrhythmia is attributable to re-entrant atrial flutter, the vector is preferably delivered locally to the right atrial myocardium of the animal (e.g. to the crista terminalis), and is more preferably delivered in a sustained-release manner. Delivery of the vector to a myocardial tissue can be effected by implanting a device (e.g. an implantable device comprising an electrode, such as a cardiac rhythm modulator or pacemaker) having a surface coated with a matrix comprising the vector in close proximity to the myocardial tissue. Preferably, the matrix is biodegradable and thereby delivers the vector to the tissue in a sustained-release manner.

The implantable device can be one which is made and used for the sole purpose of delivering the reverse gene therapy vector to the animal, or the device can be one which is applied to the surface of or inserted within the body of the animal for a purpose other than merely delivering the reverse gene therapy vector to the animal. By way of example, the implantable device can be a plurality of microspheres which comprise the reverse gene therapy vector and which are implanted into the body of the animal for the sole purpose of delivering the vector to the animal. Further by way of example, the implantable device can be a pacemaker having a surface coated with a matrix comprising the reverse gene therapy vector; the pacemaker is implanted in the vicinity of the animal's heart, both to modulate the animal's heartbeat when necessary and to deliver the vector to a cardiac tissue or to another tissue in close proximity to or in fluid communication with the coated surface of the pacemaker.

The reverse gene therapy vector can be incorporated into a coating of virtually any medical device. The coated devices provide a convenient means for local administration of the vector. For example, the vector can be incorporated into coatings for degradable and non-degradable sutures, orthopedic prostheses such as supporting rod implants, joint prostheses, pins for stabilizing fractures, bone cements and ceramics, tendon reconstruction implants, prosthetic implants, cardiovascular implants such as heart valve prostheses, pacemaker components, defibrillator components, angioplasty devices, intravascular stents, acute and in-dwelling catheters, ductus arteriosus closure devices, implants deliverable by cardiac catheters such as atrial and ventricular septal defect closure devices, urologic implants such as urinary catheters and stents, neurosurgical implants such as neurosurgical shunts, ophthalmologic implants such as lens prosthesis, thin ophthalmic sutures, and corneal implants, dental prostheses, internal and external wound dressings such as bandages and hernia repair meshes, pacemakers and other cardiac rhythm modulation devices, cardiac electrode leads, and other devices and implants, as will be apparent to the skilled artisan.

The reverse gene therapy compositions and methods described herein can be used to transforms cells located outside the body of the animal or cells located within the body of an animal. Following transformation of cells outside the body of the animal, the cells can be cultured, returned to the body of the same animal, or administered to the body of another animal of the same or different species, using substantially any known or subsequently developed method.

When the reverse gene therapy vector is delivered in the form of a particle which comprises the vector, the particle can be substantially any size. Preferably, the particle is a microparticle having a diameter less than about 900 micrometers, and preferably less than about 500 micrometers. Even more preferably, the particle is a nanoparticle having a diameter less than about 1 micrometer, and preferably less than about 600 nanometers. The vector can be present only on the surface of the particles, only at an interior portion of the particles, only in one or more layers of material in the particle, or throughout the particle. The particle preferably comprises a biocompatible material, and more preferably comprises a biodegradable material such as a polylactate-polyglycolate copolymer. Of course, substantially any known biocompatible polymeric or non-polymeric material can be used to form the particles, so long as at least a portion of the vector in or on the particle can be taken up by a cell which contacts the particle or is in fluid communication with the particle.

Cellular uptake of the gene therapy vector described herein can be enhanced by incorporating a specific cell surface receptor protein into the vector (e.g. fibroblast growth factor (FGF) or transferrin). Intracellular processing of the plasmid DNA within a lysosomal or endosomal compartment within the cell can be modulated by incorporating a lysosomotropic agent (e.g. sucrose or chloroquine) in order to reduce intracellular nuclease-mediated hydrolysis of the nucleic acid of the vector.

The reverse gene therapy vector preferably comprises a condensing agent. Condensation of DNA using polycations such as polylysine has also been demonstrated to enhance plasmid transfection by facilitating cell entry, possibly by encouraging nanoparticulate formation and protecting the DNA from nuclease mediated hydrolysis both extracellularly and within intracellular lysosomal or endosomal compartments. A preferred condensing agent is the polycation, polylysine.

The chemical identity of the condensing agent is not critical. The ability of a condensing agent to condense DNA or another nucleic acid or nucleic analog can be assessed using numerous methods known in the art. Effective amounts of such condensing agents can similarly be determined using these methods. For example, DNA condensation can be measured by comparing the kinetics in solution of condensed DNA and uncondensed DNA, and then further comparing the kinetics in the presence of a surfactant such as a detergent. It can also be measured by changes in the surface $\zeta$-potential of the DNA in solution (Wolfert et al., 1996, Human Gene Therapy 7:2123–33), or by visualizing the DNA using an electron microscope (Laemmli, 1975, Proc. Natl. Acad. Sci. USA 72:4288–4292) or an atomic force microscope (Wolfert et al., 1996, Gene Therapy 3:269–273).

One preferred family of condensing agents is the polylysines. Polylysines are polypeptides of varying lengths, comprising (e.g. primarily or exclusively) lysine residues, which are positively charged at human physiological blood pH. The lysine residues can be D-lysine residues, L-lysine residues, or a mixture of the two enantiomers; poly-L-lysine is preferred. Polylysine has been demonstrated to be an efficacious DNA condensing agent (Laemmli, 1975, Proc. Natl. Acad. Sci. USA 72:4288–4292; Wolfert et al., 1996, Gene Therapy 3:269–273). The polylysines which are useful as condensing agents in the compositions and methods described herein include all variants of polylysine, regardless of length, linear, branched, or cross-linked structure, conformation, isomerization, or chemical modification, that are capable of condensing DNA or other polyanionic bioactive agents. Exemplary chemical modifications include methylation (Bello et al., 1985, J. Biomol. Struct. Dyn. 2:899–913) and glycosylation (Martinez-Fong et al., 1994, Hepatology 20:1602–1608). Such modifications can be made before or after synthesis of the polylysine. Other condensing agents which can be used to condense DNA and other nucleic acids include elemental cations, particularly divalent cations such as $Mg^{2+}$ or $Ca^{2+}$. Such cations can, for example, be used in the form of salts, such as $MgCl_2$ or $CaCl_2$. Other suitable elemental cations include $Co^{3+}$ (particularly in the form of cobalt hexamine, $Co(NH_3)_6^{3+}$, or cobalt pentamine). $La^{3+}$, $Al^{3+}$, $Ba^{2+}$, and $Cs^+$. These cations are generally used in the form of a salt, particularly halide salts such as chloride and bromide salts, but other salts can be used as well.

It is understood that the ordinarily skilled physician or veterinarian will determine and prescribe an effective amount of the compound to alleviate the disease or disorder in the subject. In so proceeding, the physician or veterinarian can, for example, prescribe a relatively low dose at first, subsequently increasing the dose until an appropriate response is obtained. It is further understood, however, that the specific dose level for any particular subject will depend upon a variety of factors including the activity of the specific compound employed, the age, body weight, general health, gender, and diet of the subject, the time of administration, the route of administration, the rate of excretion, any drug combination, and the severity of the disease or disorder to be alleviated.

The invention encompasses the preparation and use of pharmaceutical compositions comprising the reverse gene therapy vector as an active ingredient. Such a pharmaceutical composition can consist of the active ingredient alone, in a form suitable for administration to a subject, or the pharmaceutical composition can comprise the active ingredient and one or more pharmaceutically acceptable carriers, one or more additional ingredients, or some combination of these. Administration of one of these pharmaceutical compositions to a subject is useful for alleviating a disease or disorder in the subject, as described elsewhere in the present disclosure.

As used herein, the term "pharmaceutically acceptable carrier" means a chemical composition with which the active ingredient can be combined and which, following the combination, can be used to administer the active ingredient to a subject.

The formulations of the pharmaceutical compositions described herein can be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions is contemplated include humans and other primates, mammals including commercially relevant mammals such as cattle, pigs, horses, sheep, cats, and dogs, birds including commercially relevant birds such as chickens, ducks, geese, and turkeys, fish including farm-raised fish and aquarium fish, and crustaceans such as farm-raised shellfish.

Pharmaceutical compositions that are useful in the methods described herein can be prepared, packaged, or sold in formulations suitable for oral, rectal, vaginal, parenteral, topical, pulmonary, intranasal, buccal, ophthalmic, or another route of administration. Other contemplated formulations include projected nanoparticles, liposomal preparations, and immunologically-based formulations.

A pharmaceutical composition can be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as one-half or one-third of such a dosage.

The relative amounts of the active ingredient, the pharmaceutically acceptable carrier, and any additional ingredients in a pharmaceutical composition will vary, depending upon the identity, size, and condition of the subject treated and further depending upon the route by which the composition is to be administered. By way of example, the composition can comprise between 0.1% and 100% (w/w) active ingredient.

In addition to the active ingredient, a pharmaceutical composition can further comprise one or more additional pharmaceutically active agents. Particularly contemplated additional agents include condensing agents such as polylysine.

Controlled- or sustained-release formulations of a pharmaceutical composition can be made using conventional technology.

A formulation of a pharmaceutical composition suitable for oral administration can be prepared, packaged, or sold in the form of a discrete solid dose unit including a tablet, a hard or soft capsule, a cachet, a troche, or a lozenge, each containing a predetermined amount of the active ingredient. Other formulations suitable for oral administration include a powdered or granular formulation, an aqueous or oily suspension, or an emulsion.

As used herein, an "oily" liquid is one which comprises a carbon-containing liquid molecule and which exhibits a less polar character than water.

A tablet comprising the active ingredient can, for example, be made by compressing or molding the active ingredient, optionally with one or more additional ingredients. Compressed tablets can be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets can be made by molding, in a suitable device, a mixture of the active ingredient, a pharmaceutically acceptable carrier, and at least sufficient liquid to moisten the mixture. Pharmaceutically acceptable excipients used in the manufacture of tablets include inert diluents, granulating and disintegrating agents, binding agents, and lubricating agents. Known dispersing agents include potato starch and sodium starch glycolate. Known surface active agents include sodium lauryl sulfate. Known diluents include calcium carbonate, sodium carbonate, lactose, microcrystalline cellulose, calcium phosphate, calcium hydrogen phosphate, and sodium phosphate. Known granulating and disintegrating agents include corn starch and alginic acid. Known binding agents include gelatin, acacia, pre-gelatinized maize starch, polyvinylpyrrolidone, and hydroxypropyl methylcellulose. Known lubricating agents include magnesium stearate, stearic acid, silica, and talc.

Tablets can be non-coated or they can be coated using known methods to achieve delayed disintegration in the gastrointestinal tract of a subject, thereby providing sustained release and absorption of the active ingredient. By way of example, a material such as glyceryl monostearate or glyceryl distearate can be used to coat tablets. Further by way of example, tablets can be coated using methods described in U.S. Pat. Nos. 4,256,108; 4,160,452; and 4,265,874 to form osmotically-controlled release tablets. Tablets can further comprise a sweetening agent, a flavoring agent, a coloring agent, a preservative, or some combination of these in order to provide pharmaceutically elegant and palatable preparation.

Hard capsules comprising the active ingredient can be made using a physiologically degradable composition, such as gelatin. Such hard capsules comprise the active ingredient, and can further comprise additional ingredients including, for example, an inert solid diluent such as calcium carbonate, calcium phosphate, or kaolin.

Soft gelatin capsules comprising the active ingredient can be made using a physiologically degradable composition, such as gelatin. Such soft capsules comprise the active ingredient, which can be mixed with water or an oil medium such as peanut oil, liquid paraffin, or olive oil.

Liquid formulations of a pharmaceutical composition which are suitable for oral administration can be prepared, packaged, and sold either in liquid form or in the form of a dry product intended for reconstitution with water or another suitable vehicle prior to use.

Liquid suspensions can be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions can further comprise one or more additional ingredients including suspending agents, dispersing or wetting agents, emulsifying agents, demulcents, preservatives, buffers, salts, flavorings, coloring agents, and sweetening agents. Oily suspensions can further comprise a thickening agent. Known suspending agents include sorbitol syrup, hydrogenated edible fats, sodium alginate. polyvinylpyrrolidone, gum tragacanth, gum acacia, and cellulose derivatives such as sodium carboxymethylcellulose, methylcellulose, hydroxypropylmethylcellulose. Known dispersing or wetting agents include naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include lecithin and acacia. Known preservatives include methyl, ethyl, or n-propyl-para- hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Powdered and granular formulations of a pharmaceutical preparation can be prepared using known methods. Such formulations can be administered directly to a subject, used, for example, to form tablets, to fill capsules, or to prepare an aqueous or oily suspension by addition of an aqueous or oily vehicle thereto. Each of these formulations can further comprise one or more of dispersing or wetting agent, a suspending agent, and a preservative. Additional excipients, such as fillers and sweetening, flavoring, or coloring agents, can also be included in these formulations.

A pharmaceutical composition can also be prepared, packaged, or sold in the form of oil-in-water emulsion or a water-in-oil emulsion. The oily phase can be a vegetable oil such as olive or arachis oil, a mineral oil such as liquid paraffin, or a combination of these. Such compositions can further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions can also contain additional ingredients including, for example, sweetening or flavoring agents.

A pharmaceutical composition can be prepared, packaged, or sold in a formulation suitable for rectal administration. Such a composition can be in the form of, for example, a suppository, a retention enema preparation, and a suspension for rectal or colonic irrigation.

Suppository formulations can be made by combining the active ingredient with a non-irritating pharmaceutically acceptable excipient which is solid at ordinary room temperature (i.e. about 20° C.) and which is liquid at the rectal temperature of the subject (i.e. about 37° C. in a healthy human). Suitable pharmaceutically acceptable excipients include cocoa butter, polyethylene glycols, and various glycerides. Suppository formulations can further comprise various additional ingredients including antioxidants and preservatives.

Retention enema preparations or suspensions for rectal or colonic irrigation can be made by combining the active ingredient with a pharmaceutically acceptable liquid carrier. As is known in the art, enema preparations can be administered using, and can be packaged within, a delivery device adapted to the rectal anatomy of the subject. Enema preparations can further comprise various additional ingredients including antioxidants and preservatives.

A pharmaceutical composition can be prepared, packaged, or sold in a formulation suitable for vaginal administration. Such a composition can be in the form of, for example, a suppository, an impregnated or coated vaginally-insertable material such as a tampon, a douche preparation, or a suspension for vaginal irrigation.

Methods for impregnating or coating a material with a chemical composition are known in the art, and include methods of depositing or binding a chemical composition onto a surface, methods of incorporating a chemical composition into the structure of a material during the synthesis of the material (i.e. such as with a physiologically degradable material), and methods of absorbing an aqueous or oily suspension into an absorbent material, with or without subsequent drying.

Douche preparations or suspensions for vaginal irrigation can be made by combining the active ingredient with a pharmaceutically acceptable liquid carrier. As is known in the art, douche preparations can be administered using, and can be packaged within, a delivery device adapted to the vaginal anatomy of the subject. Douche preparations can further comprise various additional ingredients including antioxidants, antibiotics, antifungal agents, and preservatives.

As used herein, "parenteral administration" of a pharmaceutical composition includes any route of administration characterized by physical breaching of a tissue of a subject and administration of the pharmaceutical composition through the breach in the tissue. Parenteral administration thus includes administration of a pharmaceutical composition by injection of the composition, by application of the composition through a surgical incision, by application of the composition through a tissue-penetrating non-surgical wound, and the like. In particular, parenteral administration is contemplated to include subcutaneous, intraperitoneal, intravenous, intraarterial, intramuscular, or intrasternal injection and intravenous, intraarterial, or kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations can be prepared, packaged, or sold in a form suitable for bolus administration or for continuous administration. Injectable formulations can be prepared, packaged, or sold in unit dosage form, such as in ampules or in multi-dose containers containing a preservative. Formulations for parenteral administration include suspensions, emulsions in oily or aqueous vehicles, pastes, and implantable sustained-release or biodegradable formulations. Such formulations can further comprise one or more additional ingredients including suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions can be prepared, packaged, or sold in the form of a sterile injectable aqueous or oily suspension. This suspension can be formulated according to the known art, and can comprise, in addition to the active ingredient, additional ingredients such as the dispersing agents, wetting agents, or suspending agents described herein. Such sterile injectable formulations can be prepared using a non-toxic parenterally-acceptable diluent or solvent, such as water or 1,3-butane diol, for example. Other acceptable diluents and solvents include Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation can comprise pharmaceutically acceptable polymeric or hydrophobic materials such as an emulsion, an ion exchange resin, a sparingly soluble polymer, or a sparingly soluble salt.

Formulations suitable for topical administration include liquid or semi-liquid preparations such as liniments, lotions, oil-in-water or water-in-oil emulsions such as creams, ointments or pastes, and suspensions. Topically-administrable formulations can, for example, comprise from about 1% to about 10% (w/w) active ingredient, although the concentration of the active ingredient can be as high as the solubility limit of the active ingredient in the solvent. Formulations for topical administration can further comprise one or more of the additional ingredients described herein.

A pharmaceutical composition can be prepared, packaged, or sold in a formulation suitable for pulmonary administration via the buccal cavity. Such a formulation can comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant can be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant can constitute 50 to 99.9% (w/w) of the composition, and the active ingredient can constitute 0.1 to 20% (w/w) of the composition. The propellant can further comprise additional ingredients such as a liquid non-ionic or solid anionic surfactant or a solid diluent (preferably having a particle size of the same order as particles comprising the active ingredient).

Pharmaceutical compositions formulated for pulmonary delivery can also provide the active ingredient in the form of droplets of a solution or suspension. Such formulations can be prepared, packaged, or sold as aqueous or dilute alcoholic suspensions, optionally sterile, comprising the active ingredient, and can conveniently be administered using any nebulization or atomization device. Such formulations can further comprise one or more additional ingredients including a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition.

Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares.

Formulations suitable for nasal administration can, for example, comprise from about as little as 0.1% (w/w) and as much as 100% (w/w) of the active ingredient, and can further comprise one or more of the additional ingredients described herein.

A pharmaceutical composition can be prepared, packaged, or sold in a formulation suitable for buccal administration. Such formulations can, for example, be in the form of tablets or lozenges made using conventional methods, and can, for example, 0.1 to 20% (w/w) active ingredient, the balance comprising an orally dissolvable or degradable composition and, optionally, one or more of the additional ingredients described herein. Alternatively, formulations suitable for buccal administration can comprise a powder or an aerosolized or atomized suspension comprising the active ingredient. Such powdered, aerosolized, or aerosolized formulations, when dispersed, preferably have an average particle or droplet size in the range from about 0.1 to about 200 nanometers, and can further comprise one or more of the additional ingredients described herein.

A pharmaceutical composition can be prepared, packaged, or sold in a formulation suitable for ophthalmic administration. Such formulations can, for example, be in the form of eye drops including, for example, a 0.1–1.0% (w/w) suspension of the active ingredient in an aqueous or oily liquid carrier. Such drops can further comprise buffering agents, salts, or one or more other of the additional ingredients described herein. Other ophthalmalmically-administrable formulations which are useful include those which comprise the active ingredient in microcrystalline form or in a liposomal preparation.

As used herein, "additional ingredients" include one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which can be included in the pharmaceutical compositions are known in the art and described, for example in Genaro, ed., 1985, *Remington's Pharmaceutical Sciences*, Mack Publishing Co., Easton, Pa., which is incorporated herein by reference.

Definitions

As used herein, each of the following terms has the meaning associated with it in this section.

The articles "a" and "an" are used herein to refer to one or to more than one (i.e. to at least one) of the grammatical object of the article. By way of example. "an element" means one element or more than one element.

By "nucleic acid" is meant any homopolymer or heteropolymer of deoxyribonucleosides, ribonucleosides, or nucleoside analogs. The nucleotide analogs can be any compound known in the art to be or subsequently discovered to be useful as a structural or functional analog of a ribonucleoside or a deoxyribonucleoside. Nucleotide analogs include nucleotides comprising bases other than the five biologically occurring bases (adenine, guanine, thymine, cytosine and uracil). The monomers of the nucleic acid can be connected by phosphodiester linkages or modified linkages such as phosphotriester, phosphoramidate, siloxane, carbonate, carboxymethyl ester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages.

A nucleic acid "encodes" an RNA or protein product if the RNA or protein product is formed by transcription or by both transcription and translation, respectively, of the nucleic acid or of a reverse transcript of the nucleic acid when the nucleic acid is RNA.

A nucleic acid "expression construct" is a nucleic acid which encodes an RNA or protein product which is formed upon transcription or upon transcription and translation of the nucleic acid. RNA expression constructs which can be directly translated to generate a protein product, or which can be reverse transcribed and either transcribed or transcribed and translated to generate an RNA or protein product, respectively, are also included within this definition.

"Naked" DNA refers to a nucleic acid vector, generally DNA, but alternatively comprising another nucleic acid, which is delivered to a cell in a suspension that does not comprise a matrix, a virus vector, or a similar structure which contains the nucleic acid. Naked DNA vectors encompass nucleic acid vectors which comprise agents (e.g. condensing agents or amphipathic carriers), in addition to the nucleic acid, which promote uptake of the nucleic acid by cells.

By describing two polynucleotides as "operably linked" with one another is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked with the coding region of a gene is able to promote transcription of the coding region.

As used herein, the term "promoter/regulatory sequence" means a nucleic acid sequence which is required for expression of a gene product operably linked with the promoter/regulator sequence. In some instances, this sequence can be the core promoter sequence and in other instances, this sequence can also include an enhancer sequence and other regulatory elements which are required for expression of the gene product. The promoter/regulatory sequence can, for example, be one which expresses the gene product in a tissue specific manner.

A "constitutive" promoter is one which catalyzes initiation of DNA transcription at approximately the same level, regardless of the tissue type of the cell within which it is contained.

A "tissue-specific" promoter is one which catalyzes initiation of DNA transcription at different rates in different tissue types. Generally, an 'X tissue-specific' promoter initiates DNA transcription at a greater rate in cells of tissue type X than in cells of a different tissue type.

A "physiologically responsive" promoter is one which catalyzes initiation of DNA transcription at different rates, depending on the presence, absence, or degree of a physiological state, such as the presence of a particular chemical compound or a particular histological structure.

A "pharmacological agent-specific enhancer" is a nucleic acid element which, when present in an expression construct, increases expression from the expression construct in the presence of the pharmacological agent, relative to expression from the expression construct in the absence of the pharmacological agent.

A "ribozyme" is an RNA molecule, or a molecule comprising an RNA molecule and a polypeptide molecule, which is capable of specifically catalyzing a chemical reaction, in a manner analogous to enzymatic catalysis.

As used herein, a "virus vector" is a nucleic acid-containing composition which comprises a protein which naturally occurs in a virus, wherein the composition is capable of transferring its nucleic acid into the interior of at least one type of cell when the virus vector is contacted with the cell.

A "gene therapy vector" is a composition of matter which comprises an expression construct and which can be used to deliver the expression construct to the interior of a cell.

A "therapeutic gene product" is a protein or RNA molecule which, when provided to or expressed in a diseased or wounded tissue, alleviates, prevents, or inhibits the disease, promotes healing of the wound, or prevents worsening of the wound.

An "antisense oligonucleotide" is a nucleic acid molecule (e.g. DNA, RNA, or a polymer comprising one or more nucleotide analogs), at least a portion of which is complementary to a nucleic acid which is present in a cell. The antisense oligonucleotides preferably comprise between about twelve and about fifty nucleotides. More preferably, the antisense oligonucleotides comprise between about fourteen and about thirty nucleotides. Most preferably, the antisense oligonucleotides comprise between about sixteen and about twenty-one nucleotides. The antisense oligonucleotides include phosphorothioate oligonucleotides and other modifications of oligonucleotides, as described herein. Methods for synthesizing oligonucleotides, phosphorothioate oligonucleotides, and otherwise modified oligonucleotides are known in the art (U.S. Pat. No: 5,034.506; Nielsen et al., 1991. Science 254: 1497), and each of these types of modified oligonucleotides in included within the scope of the invention.

As used herein, an "apoptosis-inducing protein" means a protein which, when expressed in a cell, causes the cell to begin, accelerate, or continue the process of programmed cell death, which is characterized by the fragmentation of the cell into membrane-bound particles that are subsequently eliminated by the process of phagocytosis.

"Local" or "localized" delivery of an agent to a cell or to a tissue of an animal refers to delivery of the agent using a method that does not deliver the agent systemically to the animal, and which preferably does not deliver any significant proportion of the agent to cells or tissue other than that to which delivery is intended. Numerous compositions and methods are known to be effective for local delivery, as described herein.

An agent is delivered to a cell or tissue "in a sustained-release manner" if the agent is administered to the cell or tissue in a formulation wherein the cell or tissue is contacted with the agent for a longer period than it would be if the agent were administered without the formulation. For example, a sustained release preparation for delivering a nucleic acid releases the nucleic acid from the preparation over time, and protects not-yet-released nucleic acid from degradation (e.g. nuclease-catalyzed degradation).

"Diseases and disorders," as used herein refer to any pathological or other undesirable and abnormal physiological condition of a cell, regardless of whether the condition is formally recognized as a 'disease.'

Cells or tissue are "affected" by a disease or disorder if the cells or tissue have an altered phenotype relative to the same cells or tissue in a subject not afflicted with the disease or disorder.

An "abnormal" animal tissue is one which, when obtained from an animal afflicted with a disease or disorder, has a phenotype which is different from the phenotype of same tissue in an animal of the same type which is not afflicted with the disease or disorder.

A "defective" protein is a protein which has an altered amino acid sequence, relative to the wild type protein, and which does not exhibit the same type or degree of activity or other property that the wild type protein exhibits.

As used herein, "alleviating" a disease or disorder means reducing the frequency or severity with which a symptom of the disease or disorder is experienced by a patient.

A "re-entry circuit" is a conduction pathway in heart tissue that does not follow the normal impulse progression route, but instead re-enters partially re-polarized tissue in a sustained abnormal cycle that results in rapid, uncontrollable heart rhythms.

The "interior portion" of a matrix is a portion of the matrix which does not contact a solvent in which the matrix is suspended or in which a device or particle coated with the matrix is suspended or immersed, at least until the matrix has at least partially biodegraded. It is understood that, in instances in which multiple layers of matrix are present, the "interior portion(s)" of the matrix can refer only to the innermost portion of the innermost layer of the matrix (i.e. the first-deposited layer) or to the inner portion of each layer of the matrix, with respect to the first-deposited layer. The interior portion of the matrix does not include the exterior surface of the matrix, but can include any and all parts of the matrix that are not exposed on the exterior surface.

A material is "biocompatible" with respect to an animal if the presence of the material in the animal is not substantially injurious to the animal. By way of example, a biocompatible material does not induce an immune response to the material when the material is implanted in the body of an animal.

A material is "biodegradable" if the material undergoes decomposition when contacted with a biological system upon implantation into an animal. The decomposition can be evidenced, for example, by dissolution, depolymerization, disintegration, or by another chemical or physical change whereby the bulk of the material in the biological system is reduced over time. Such decomposition can be, but is not necessarily, catalyzed by a component of the biological system (e.g. an enzyme).

A material is "in fluid communication" with a cell or tissue if the material is in contact with a fluid which normally contacts the cell or tissue, either in vitro or in vivo. Examples of materials in fluid communication with a cell or tissue include a material deposited, suspended, or dissolved in a tissue culture medium in which the cell or tissue is maintained, a material deposited, suspended, or dissolved in a body fluid which normally contacts the cell or tissue in an animal, and a material which physically contacts the cell or tissue.

As used herein, the term "condensing agent" and grammatical forms thereof generally refers to molecules such as polycationic polymers and elemental cations that, because of their size or for some other reason, are able to condense nucleic acids. A non-limiting list of polycationic condensing agents which are suitable for condensing nucleic acids such as DNA can be found in Lasic (1997, In: Gene Delivery, Lipsows, Ed., CRC Press, Boca Raton, Fla., pp. 33–37 and 56–61).

A nucleic acid is "condensed" if, when combined with a condensing agent, the nucleic acid exhibits reduced nuclease susceptibility, decreased hydrodynamic diameter, a more geometrically compact conformation, or reduced susceptibility to oxidation. Condensation of nucleic acids has been described in the prior art (e.g. using polylysine) and is known.

A "particle" or "particulate formulation" means an object, or plurality of such objects, having geometric dimensions compatible with injection, cellular ingestion, or mucous membrane penetration. Thus, such a particulate formulation typically comprises, or preferably consists essentially of, generally spherical or ellipsoid particles having a maximal geometric dimension of about 50 microns, preferably less than about one micron, and more preferably, from about 100 nanometers to 500 nanometers.

A "bulk material" or "bulk formulation" means a monolithic object, having geometric dimensions in excess of those compatible with injection, cellular ingestion, or mucous membrane penetration. Such bulk formulations typically have one or more geometric dimensions in excess of 50 microns. Bulk materials can, for example, be provided in the form of spheres, irregular shapes, sheets, needles, bars, and the like.

The "hydrodynamic diameter" of an object such as a molecule or a particle refers to the diameter of an imaginary sphere which is traced by rotating the object in all directions around its center of mass. The hydrodynamic diameter can be thought of roughly as the 'effective size' of an object rotating rapidly in space or in solution. By way of example, the hydrodynamic diameter of a sphere is the actual diameter of the sphere, and the hydrodynamic diameter of a rigid rod-shaped object is the length of the object along its longest axis (i.e. the length of the rod).

An "implantable device" means a particle or other object which can be entirely or partially inserted into the body of an animal. Implantable devices thus include particles which, when applied topically to a surface of the animal body, are capable of being taken up by a tissue or cell of the animal. The means by which the particle or other object is inserted into the animal body is not critical, and includes, for example, swallowing, inhalation, injection, topical application, physical penetration, insertion into an incision made in the animal body, and the like.

The invention is now described with reference to the following Examples. These Examples are provided for the purpose of illustration only and the invention should in no way be construed as being limited to these Examples, but rather should be construed to encompass any and all variations which become evident as a result of the teaching provided herein.

EXAMPLE 1

Ibutilide Controlled Release Matrices for Preventing Re-entrant Atrial Flutter in Dogs In the experiments described in this Example, the Y-atriotomy model for re-entrant flutter in dogs, as described (Labhasetwar et al., 1998, J. Cardiovasc. Pharmacol. 31:449–455) was used to demonstrate the efficacy of sustained release of ibutilide from a right atrial epicardial implant for alleviating re-entrant atrial flutter.

Ibutilide sustained release matrices were made using a multi-layer polyurethane solvent evaporation technique to coat an epicardial pacing electrode. Inducibility of atrial flutter upon burst atrial pacing was investigated in dogs which had a coated electrode implanted therein, compared with dogs which had a non-coated electrode implanted therein. As indicated in FIG. 1, inducibility of atrial flutter was significantly reduced in dogs which had a coated electrode implanted therein ("Ibutilide Cont. Rel" in FIG. 1). The rate of release of ibutilide from the electrode in these dogs was approximately 2.4 micrograms per hour per millimeter of electrode length. No significant inhibition of inducibility of atrial flutter was observed in dogs which had non-coated electrodes implanted therein or in dogs which were systemically administered a dose of ibutilide equivalent to that provided by the polymer. Electrophysiologic studies demonstrated that atrial ibutilide delivery did not significantly affect ventricular electrophysiologic parameters.

The results of the studies described in this Example demonstrated the site-specific therapy directed at the right atrial myocardium can be effective to suppress re-entrant atrial flutter.

EXAMPLE 2

HERG Gene Therapy of Re-Entrant Atrial Flutter in a Dog Model

The experiments described in this Example demonstrate that DNA-containing biodegradable polymeric microparticle and nanoparticles are useful for delivery of nucleic acid vectors to animal cells.

A reverse gene therapy method is used to locally deliver a nucleic acid vector comprising a defective HERG protein to the right atrium of dogs in order to effect site specific overexpression of HERG (A561V) at that site.

The nucleic acid vector is delivered in the form of a plasmid suspended in nanoparticles of a polylactic-polyglycolic acid (PLGA) copolymer having poly-L-lysine (PLL) incorporated therein. The plasmid DNA is in a condensed form. Prior to using the nucleic acid vector encoding defective HERG, a reporter vector comprising a nucleic acid encoding a bacterial β-galactosidase or a luciferase operably linked with a CMV promoter is used to assess the level and localization of expression effected by PLGA/PLL nanoparticle delivery of the vector. Nucleic acid vector bioavailability distribution to distal sites is assessed using PCR. The dog model of cardiac arrhythmia is based upon re-entrant atrial flutter which is induced after a Y-atriotomy incision, as described (Frame, 1996, Cardiol. Clin. 14:471–481).

Formation of DNA-PLGA Particles

The plasmid described in this Example was formulated for sustained release by suspending it a biodegradable polymer microparticle that could be injected into a specific tissue site in the canine atrial myocardium.

The microparticles were formed using an oil-in-water emulsion of a PLGA copolymer. Sonication of the emulsion (e.g. to control particle size) was avoided to minimize damage to the plasmid. Instead, a "salting-out" technique was used to control the particle size. PLGA (3 milligrams per milliliter) was suspended in chloroform, and a small volume (ca. 100 microliters) of an aqueous plasmid DNA suspension (comprising about 10 milligrams per milliliter DNA) was added to this, while vortexing the mixture at 30,000 rotations per minute at 0° C. for one minute, to generate an initial emulsion.

The initial emulsion was combined with an aqueous solution comprising either no or 1 molar $CaCl_2$ and (0.1–0.5% v/v) polyvinyl alcohol (PVA) as an emulsifier. This mixture was vortexed at 0° C. for one minute to generate a second emulsion. The mixture was ultracentrifuged to separate microparticles, and the microparticles were repeatedly re-suspended and ultracentrifuged to remove non-incorporated plasmid. Particle size analysis was performed using a laser light scattering apparatus (NICOMP; Brookhaven Labs, New York, N.Y.), and particle morphology was assessed by scanning electron microscopy. Plasmid-containing microparticles having an average diameter of about 2.7 micrometers were made when 1 molar $CaCl_2$ was included in the PVA-containing phase; microparticles having an average diameter of about 4.0 micrometers were made when the PVA-containing phase did not contain $CaCl_2$.

Figure 2:
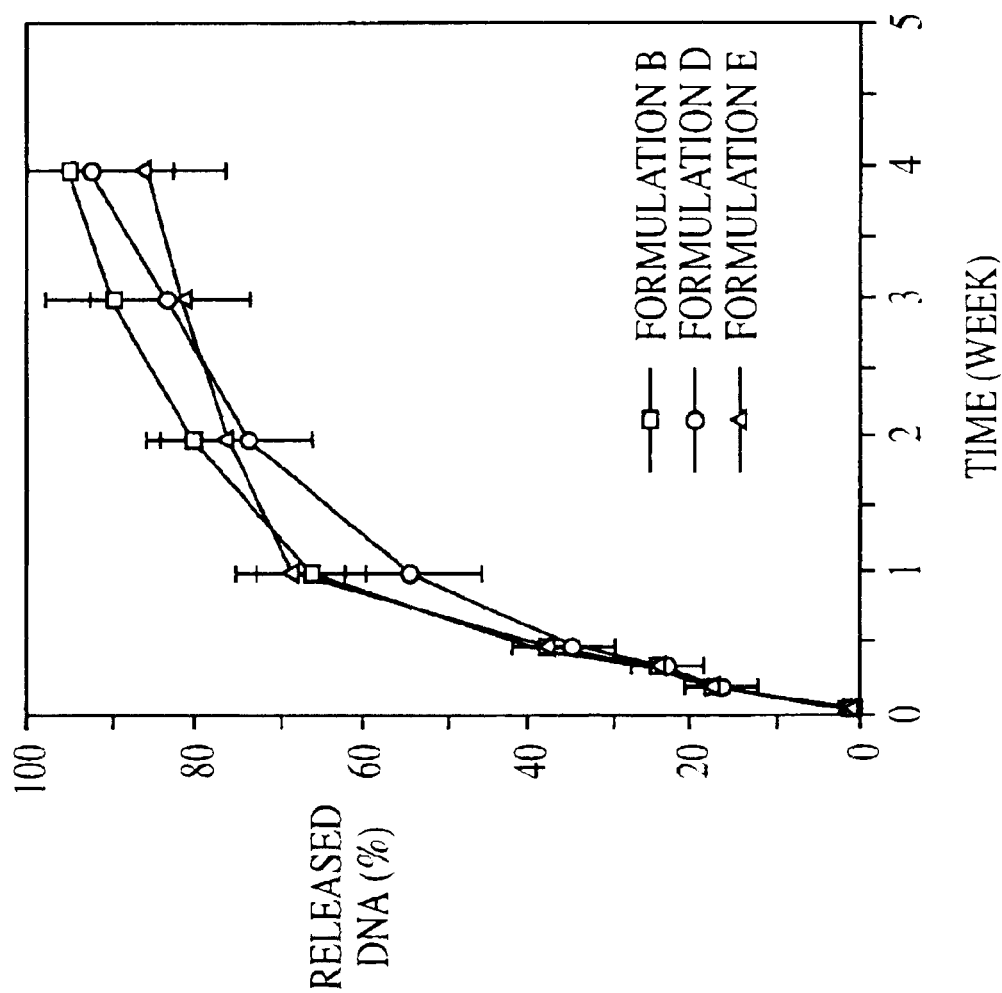
FIG. 2 is a graph which indicates the proportion of DNA released from PLGA copolymer microparticles, as described herein.

The rate of release of DNA from the microparticles was investigated by incubating the particles in vitro in a solution comprising 0.1 molar Tris buffer at pH 7.4, 0.01 molar EDTA, and these data demonstrated that the DNA entrapped within the microparticles was made available with an initial burst phase of release, followed by an exponentially declining release rate. Nearly complete release of DNA from the microparticles was effected by 30 days incubation, as indicated in FIG. 2. In FIG. 2, formulation B comprised microparticles initially consisting of about 2% (w/w) plasmid, formulation D comprised microparticles initially consisting of 5% (w/w) plasmid, and formulation E comprised microparticles initially consisting of 11% (w/w) plasmid. No evidence of plasmid DNA fragmentation was detected by agarose gel electrophoresis of DNA released from the microparticles.

Figure 3:
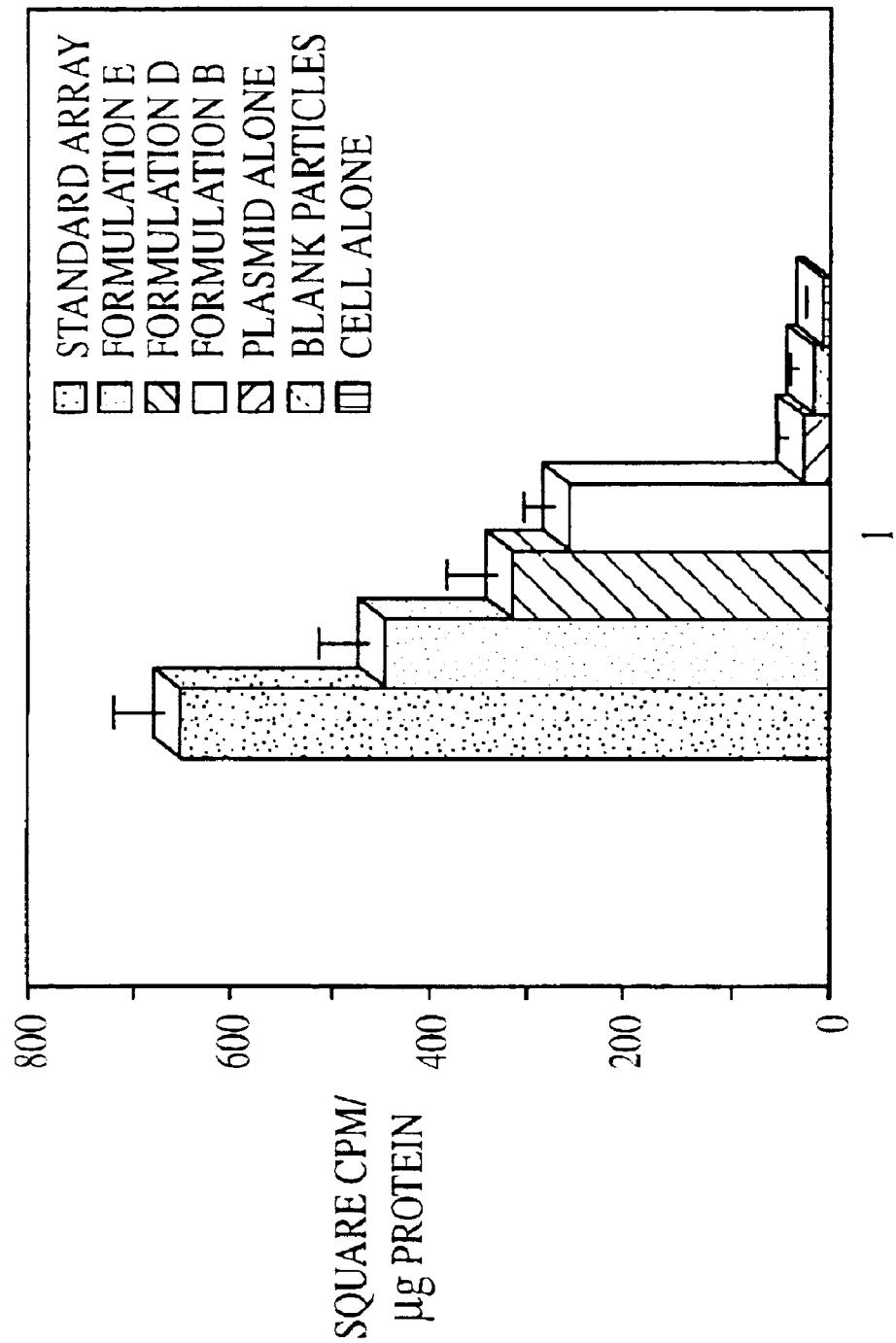
FIG. 3 is a bar graph which indicates luciferase activity in type 293 cells transformed using DNA-containing PLGA copolymer microparticles, as described herein.

Transformation studies using a plasmid encoding a luciferase protein were performed by contacting type 293 cells with the plasmid. The plasmid was incorporated into DNA-microparticles as described herein, using $CaCl_2$. As indicated in FIG. 3, the $CaCl_2$ microparticle synthesis protocol resulted in significantly enhanced transfection, and a dose-response relationship was evident, with respect to the amount of DNA loaded into the microparticles.

Formation of DNA-PLGA-PLL Nanoparticles

The plasmid described in this Example was formulated for sustained release by suspending it a biodegradable polymer nanoparticle that could be injected into a specific tissue site in the canine atrial myocardium.

In these experiments nanoparticles having submicrometer diameters were made, the nanoparticles comprising PLGA and PLL. Nanoparticle formulations procedures were identical to those described above for preparation of microparticles, with the following changes. PLL having a molecular weight of 4000 was added to the PVA-containing phase at a concentration of 0.5 milligrams per 500 milligrams PVA in 10 millimolar Tris buffer adjusted to pH 7.4 using HCl and containing 10 micromolar EDTA. The second emulsion was ultracentrifuged, rinsed, and freeze-dried.

Figure 4A:
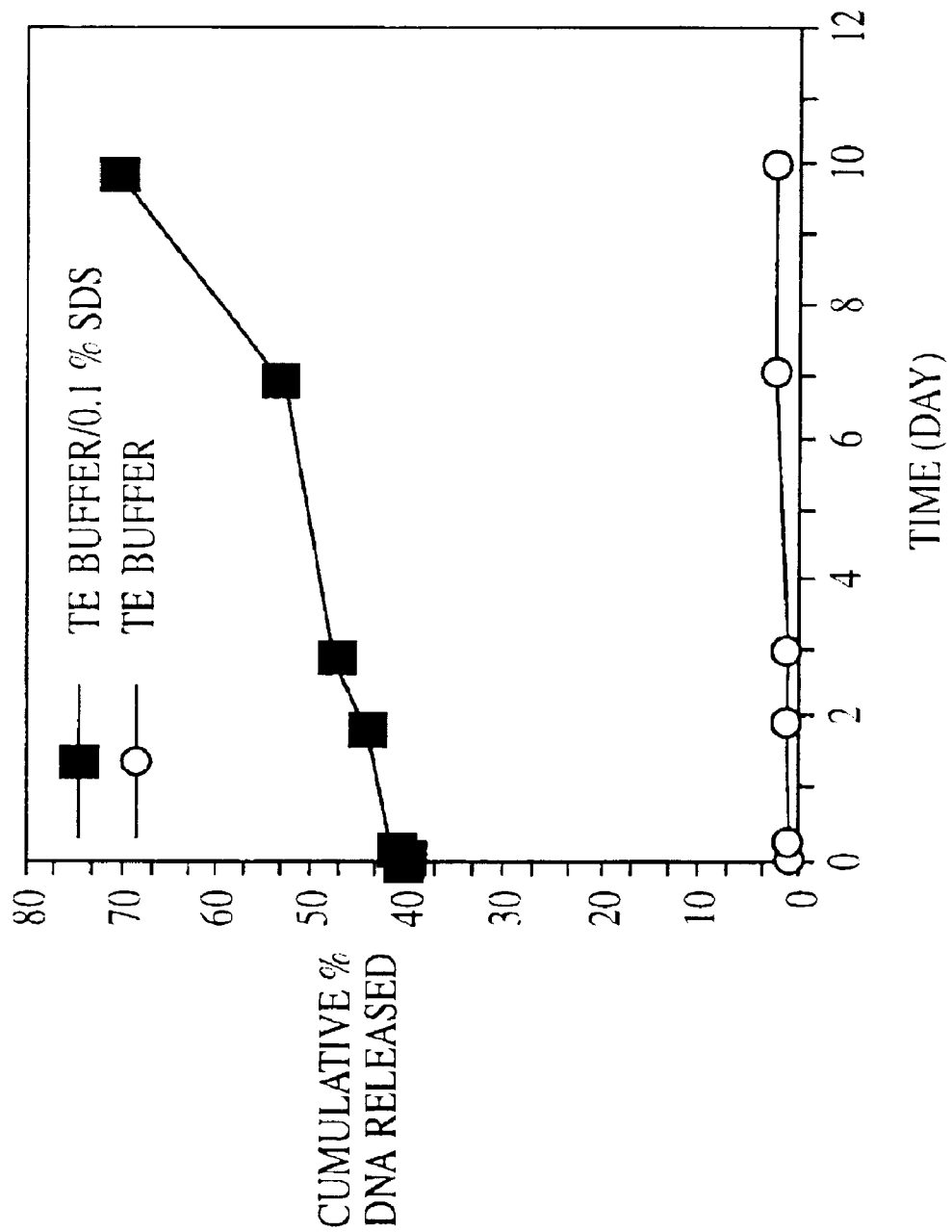
FIGS. 4A, 4B, and 4C is a trio of graphs which indicate properties of DNA-containing PLGA copolymer nanoparticles, as described herein.
Figure 4B:
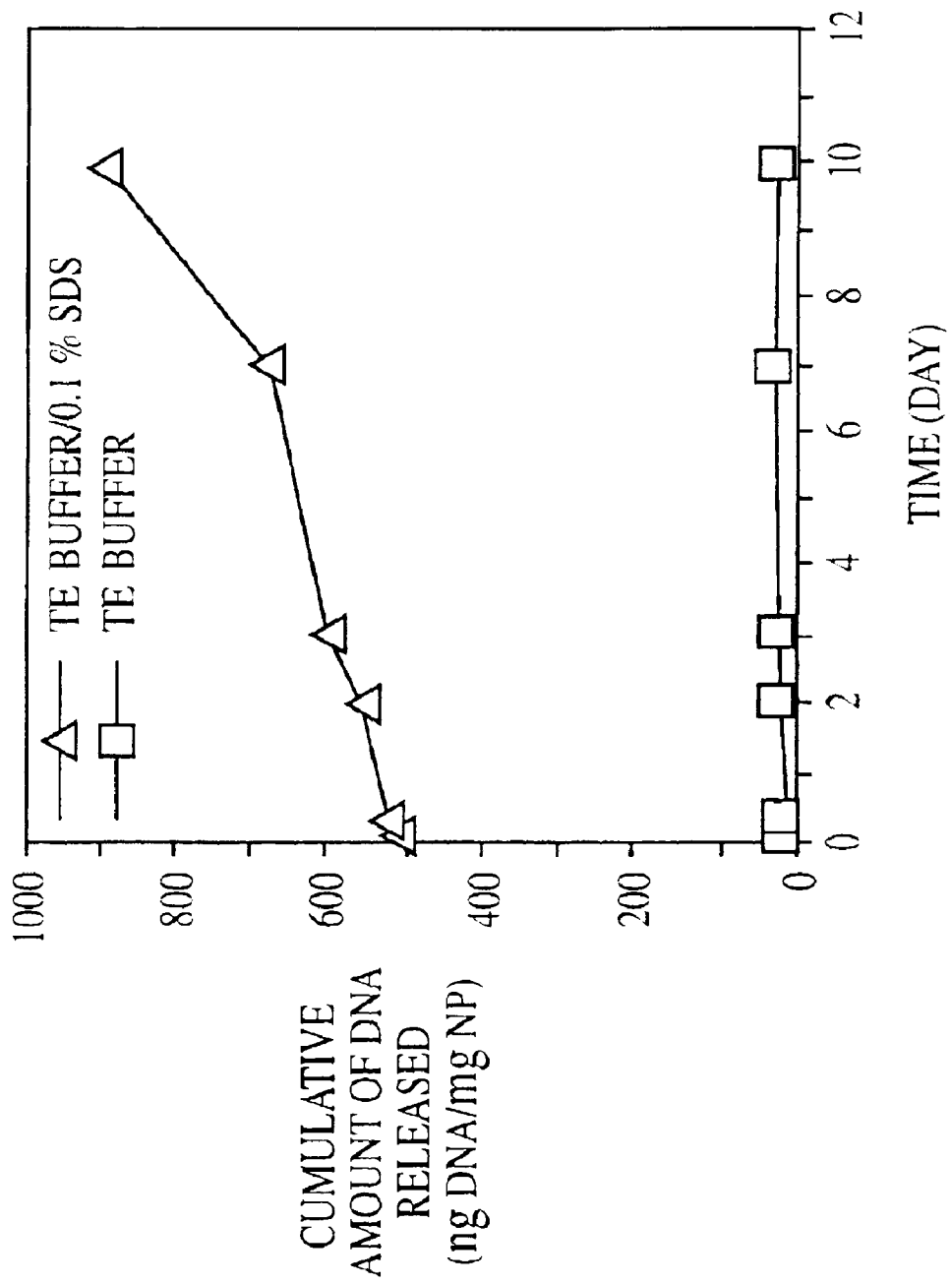

Analysis of the nanoparticles made by this method revealed that nanoparticles comprising 3% DNA, by weight, had an mean diameter of about 500 nanometers, and that more than 86% the DNA used to make the particles was incorporated into the nanoparticles. Other characterization procedures indicated that PLL condensed the plasmid DNA in the microparticles. For example, studies of DNA release from nanoparticles in the Tris-EDTA buffer indicated very slow DNA elution, as indicated in FIGS. 4A an 4B. However, if the 0.1% (w/v) sodium dodecyl sulfate was included in the Tris-EDTA buffer, the rate of DNA release from the nanoparticles was increased significantly. Further by way of example, incubation of the nanoparticles in an organic solvent ($CHCl_3$) followed by aqueous recovery of the DNA indicated that only after incubating the nanoparticles with SDS or trypsin could released DNA be detected. These observations also indicate that the plasmid was suspended in or on the nanoparticles in the form of a DNA-PLL condensate.

Comparisons with $CaCl_2$-DNA microparticles prepared as described herein and DNA-PLL-PLGA nanoparticles are indicated in Tables I and II.

TABLE I

A comparison of the physical characteristics of DNA-$CaCl_2$ microparticle and DNA-PLL-PLGA nanoparticle

| Preparation | DNA capture Efficiency[a] | Mean Particle Size | 48 hr DNA release (in TE buffer) | 48 hr DNA release (in TE Buffer + 0.1% SDS) |
|---|---|---|---|---|
| PLGA-$CaCl_2$ Microparticles | 43.3% | 2.7 μm | 20% | NM[b] |
| PLGA-PLL Microparticles | 86.3% | 476 nm | 1.7% | 44% |

Notes:
[a]DNA capture efficiency means the percentage (by weight) of the DNA used to make the particles which was incorporated into the particles.
[b]NM means not measured.

TABLE II

Size distribution and surface charge (zeta potential) of DNA-PLL-PLGA nanoparticles (pHOOK-LacZ DNA was used)

| Formulation | Particle size | zeta potential |
|---|---|---|
| PLGA | 496.5 ± 6.1 nm | −32.13 ± 1.47 mV |
| DNA/PLGA | 522.5 ± 4.7 nm | −35.01 ± 2.47 mV |
| PLGA-PLL | 510.6 ± 7.4 nm | −27.99 ± 0.70 mV |
| DNA-PLL-PLGA | 507.5 ± 8.9 nm | −38.45 ± 1.27 mV |

As is evident from Table II, incorporation of PLL into PLGA nanoparticles resulted in a more positively charged nanoparticle. However, the charge of the DNA-PLL-PLGA was significantly more negative than the charge of the PLL-PLGA particle, indicating that the DNA neutralized the charge of PLL.

Figure 4C:
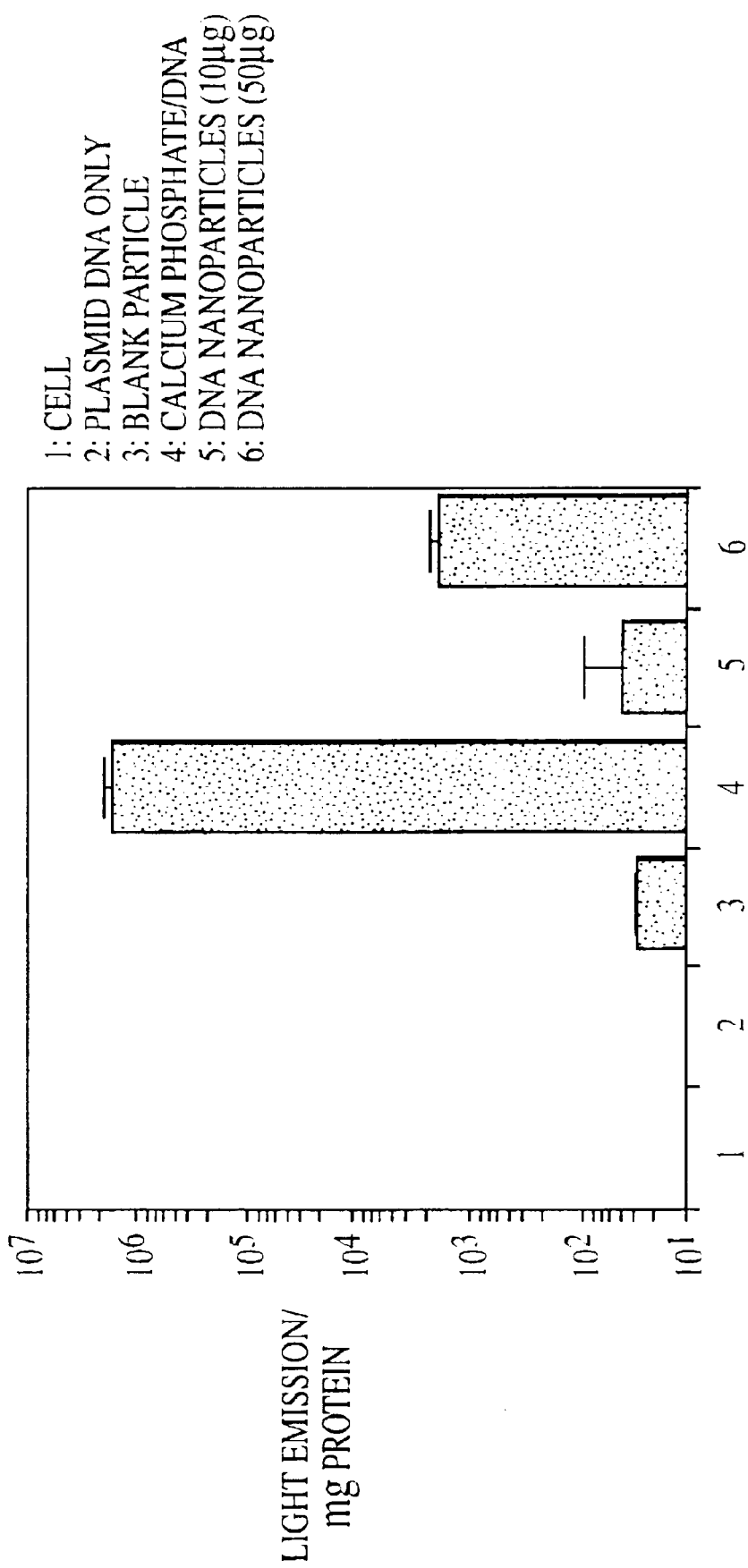

PLL-containing PLGA nanoparticles comprising a plasmid which encoded luciferase were used to transform type 293 cells. As indicated in FIG. 4C, significant enhancement of transformation after 48 hours incubation of the cells with the PLL-PLGA-DNA nanoparticle, relative to the transformation achieved using cells incubated for 48 hours with PLGA nanoparticles which did not comprise DNA.

Figure 5:
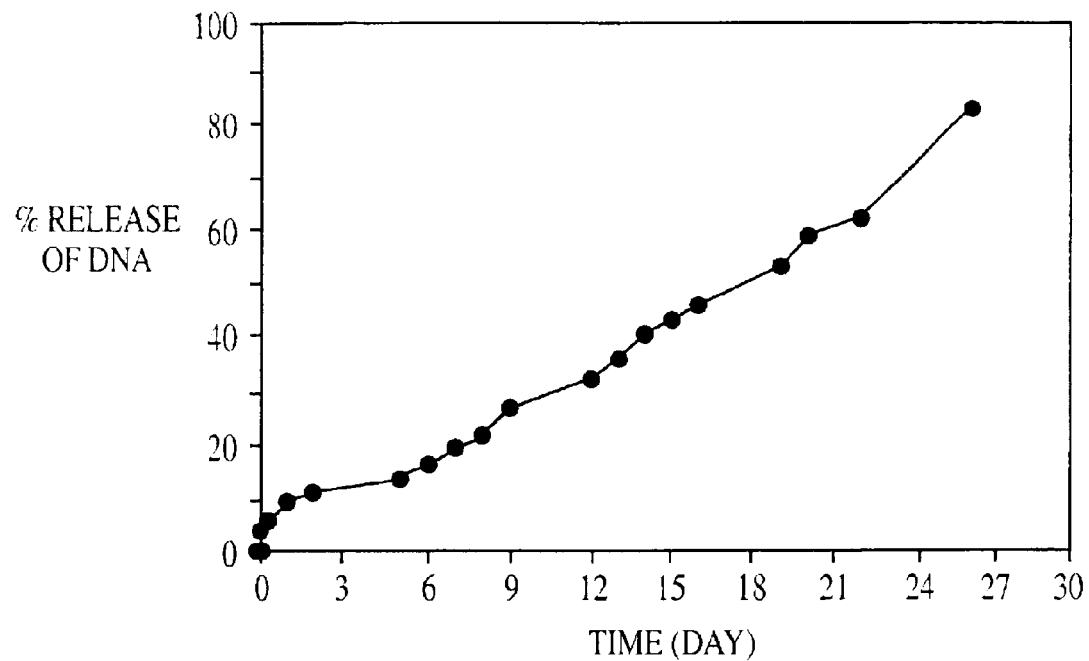
FIG. 5 is a graph which indicates in vitro release of DNA from a suture coated with a DNA-PLGA emulsion, as described herein.

DNA-PLGA Sustained Release Coatings: Suture-Based Gene Delivery and Atrial Myocardial Results Chromic sutures were coated with a DNA-PLGA emulsion, which was prepared as described herein. This coated suture was used to repair subcutaneous wounds made in rats. In vitro release kinetics of DNA from a suture coated with a DNA-PLGA polymer containing 0.5% (w/w) DNA are indicated in FIG. 5. These data indicate that, following a brief burst phase, the rate of release of DNA from the suture is nearly constant.

Figure 6:
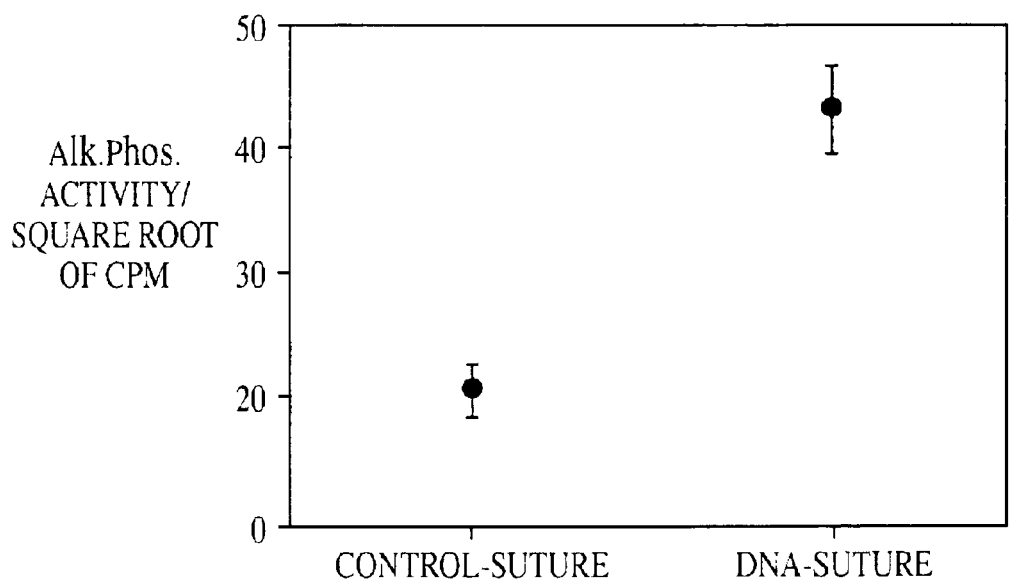
FIG. 6 is a graph which indicates alkaline phosphatase activity detected in wounded tissue obtained from wound sites closed using either a DNA-PLGA-coated suture or a non-coated (control) suture.

A chromic suture was coated with a PLGA-DNA polymer using the emulsion technique described herein. The DNA was a plasmid comprising an expression construct encoding human alkaline phosphatase. Transformation of skeletal muscle cells was demonstrated by using this coated suture to close subcutaneous skeletal muscle wound sites in rats. The amount of suture used per wound site contained approximately 250 micrograms of plasmid DNA. Tissue recovered from wound sites was assayed using known methods to determine expression of alkaline phosphatase at the site. As indicated in FIG. 6, significantly greater alkaline phosphatase activity was detected at wound sites closed using the DNA-PLGA coated suture than at wound sites closed using a suture which did not contain DNA.

Figure 7:
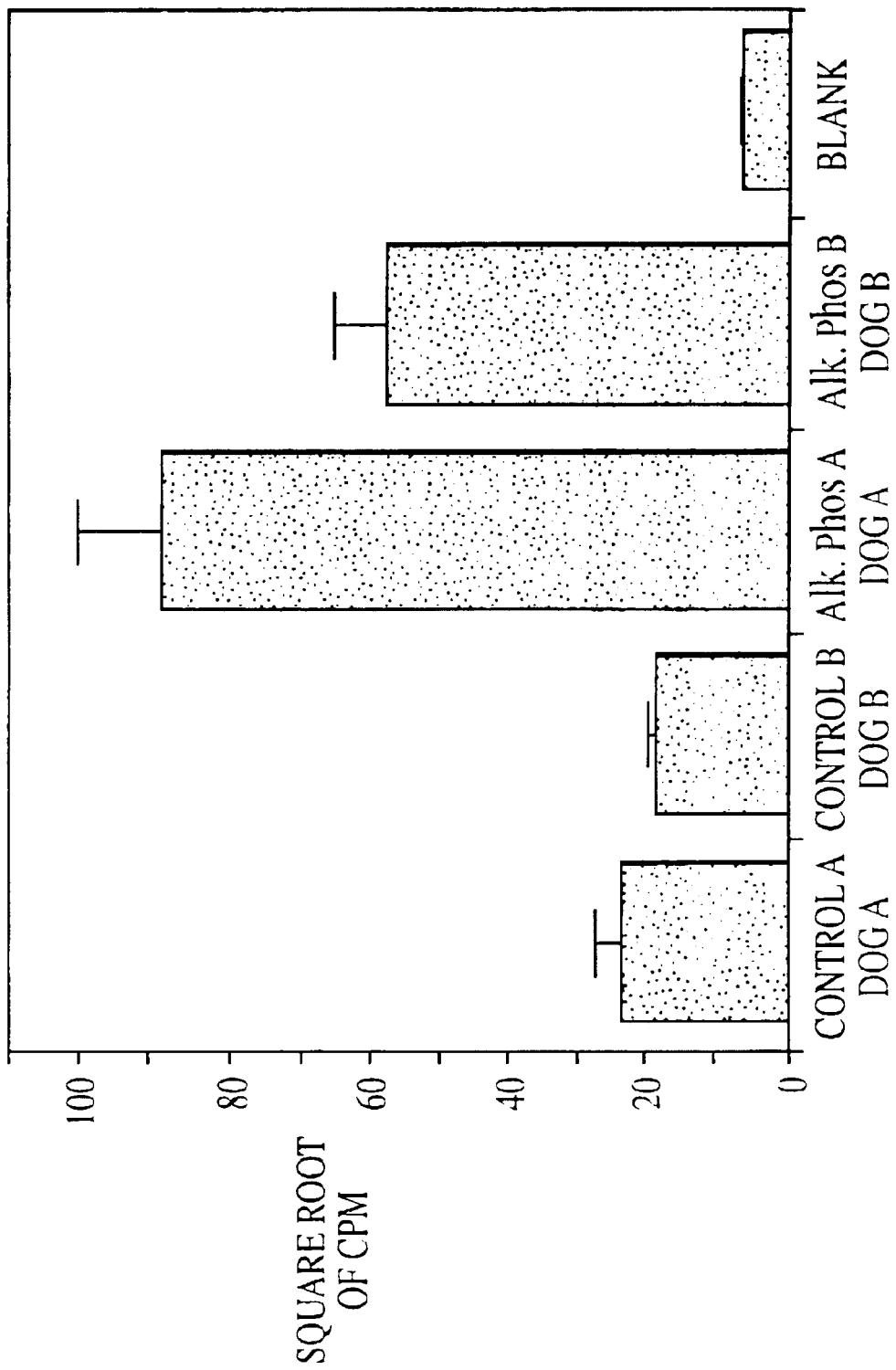
FIG. 7 is a bar graph which indicates alkaline phosphatase activity detected in atrial tissue obtained from dogs in which an atriotomy incision was made and repaired using either a DNA-PLGA-coated suture or a non-coated (control) suture. Individual dogs are designated 'A' and 'B' for each suture type. "Blank" indicates myocardial tissue not injected with DNA.

This DNA-PLGA coated suture was then used in a series of atriotomy studies to determine if the coating could be used to transform cells of the atrial myocardium. In two-dog studies, a one-centimeter atriotomy incision was made in the right atrial appendage of each of four dogs. The atriotomy incision was repaired either with the PLGA-DNA coated chromic suture or with a chromic suture which did not comprise DNA. Atrial tissue was recovered from the dogs following euthanasia. As indicated in FIG. 7, significantly greater alkaline phosphatase activity was detected in atrial tissue closed using the DNA-PLGA coated suture than in atrial tissue closed using a suture which did not contain DNA.

EXAMPLE 3

Gene Therapy Using a Cardiac Myocyte Model

The Experiments described in this Example can be used to demonstrate that a nucleic acid vector comprising an expression vector encoding the HERG (A561V) protein can be delivered to atrial myocardium cells in order to alleviate re-entrant atrial flutter.

CHO Cell Transformation Studies

Transformation of Chinese Hamster Ovary (CHO) cells in vitro is used to investigate the mechanism(s) by which the cells are transformed using DNA-PLGA-PLL nanoparticles. Transformation of CHO cells is also used to investigate the effects of nanoparticle formulation parameters (e.g. the effect of including or omitting PLL from the particles) on the steps involved in nanoparticle uptake, endosomal or lysosomal transit of the nanoparticles within the cells, and nuclear expression of vector DNA. Properties of transformed CHO cells which are assessed include histological or immunological examination of the location of vector DNA expression, enzyme activity of an enzyme encoded by the vector DNA, and assessment cell death or growth inhibition mediated by PLL or PLGA.

CHO cells are selected for several reasons. Other investigators have demonstrated successful transfection of these cells using vectors comprising mutant genes responsible for the Long QT Syndrome and CHO cells in culture (Sanguinetti et al., 1996, Proc. Natl. Acad. Sci. USA. 93:2208–2212; Sanguinetti et al., 1996, Nature 384:80–83; Sanguinetti et al., 1995. Cell 81 299–307). CHO transfection experiments are performed using DNA vectors which comprise a CMV promoter operably linked with a nucleic acid encoding the HERG (A561V) protein.

Cardiac Myocyte Transformation Studies

Primary cardiac myocytes transformation is performed using either of two candidate promoters having specificity for cardiac tissue. Transformation efficiency using a DNA vector comprising a CMV promoter, the α-myosin heavy chain (α-MyHC) promoter (Robbins, 1997, Trends Cardiovasc. Med. 7:185–191; Milano et al., 1994, Proc. Natl. Acad. Sci. USA 91. 10109–10113), or the atrial natriuretic factor (ANF) promoter (Field, Science 239:1029–1033), is determined using rat primary cardiac myocytes in culture. These latter two promoters can be inserted into the vector DNA using a recombinant methodology, as described (Robbins, 1997, Trends Cardiovasc. Med. 7:185–191; Milano et al., 1994, Proc. Natl. Acad. Sci. USA 91: 10109–10113; Field, Science 239:1029–1033). The vector DNA can further comprise a reporter nucleic acid (e.g. a cDNA encoding luciferase) or a pathological nucleic acid (e.g. a nucleic acid encoding HERG (A561V) protein).

Plasmid DNA Transfection Assays

CHO cells are used as a model cell culture system to evaluate the degree of episomal transformation, gene expression, and enzyme activity of a β-galactosidase expression construct following delivery of DNA-PLL-PLGA nanoparticles to the cells. Upon completion of these initial studies, primary rat neonatal cardiac myocyte cells in culture are used to study the efficacy of transformation of those cells using a HERG (A561V) protein expression construct in a DNA-PLL-PLGA nanoparticle.

Cell cultures in Dulbecco's Modified Eagle Medium containing 1% (v/v) fetal bovine serum and 1% (w/v) penicillin or streptomycin are approximately 25% confluent for all transfection experiments. The cell culture media are removed and replaced with fresh media containing DNA-PLL-PLGA nanoparticles dispersed therein. The nanoparticle equivalent of 10, 20, 50, or 100 micrograms of DNA is added to each culture plate in order to determine the operable range of DNA dose for the cell culture system. For comparison, a standard calcium phosphate-mediated DNA transformation is performed as a positive control. At the conclusion of each 48 hour study, transformed cells are either prepared for immunohistochemistry or cytochemistry or scraped off the culture dish for enzymatic assay of gene expression.

Transformed cells harvested from cultures are fixed for 10 minutes using a 0.5% (v/v) glutaraldehyde solution in phosphate buffered saline. The cells are rinsed and incubated for 10 minutes at room temperature (i.e. about 20° C.) with a 1 millimolar $MgCl_2$ solution in pH 7.4 phosphate buffered saline. The cells are then stained for 5 hours using an X-gal staining solution, comprising 1 milligram of X-gal per milliliter, 5 millimolar $K_3Fe(CN)_6$, 5 millimolar $K_4Fe(CN)_6$, and 1 millimolar $MgCl_2$ in pH 7.4 phosphate buffered saline. Samples are embedded in paraffin and prepared for light microscopy after post-fixation treatment with a phosphate buffered solution comprising 4% (v/v) paraformaldehyde and 0.5% (v/v) glutaraldehyde.

β-galactosidase activity in cell lysate is detected using a Galacto-Light PLUS™ chemiluminescent reporter system, as described (Jain et al., 1991. Anal. Biochem. 199:119–124). The amount of β-galactosidase activity in the sample is determined using a luminometer, and enzyme activity is normalized to account for protein content.

Immunohistochemistry is performed to localize protein expression in tissue or cells. Because reporter assays frequently underestimate the extent of transfection (Couffinhal et al., 1997, Hum. Gene Ther. 8: 929–934), immune techniques are also used to assess the degree of transfection. Fixation is performed using 10% (v/v) neutral buffered formalin, followed by either cryostat or paraffin sectioning. Sections mounted on slides are treated first with ammonium chloride or sodium borohydride to quench extraneous aldehyde groups, or with hydrogen peroxide to block endogenous peroxidase activity, and then with 2% (w/v) gelatin in phosphate buffered saline to block non-specific protein binding. The primary antibody of interest (which binds specifically with either β-galactosidase or with FLAG (see below)) is applied, followed by an appropriate secondary antibody (i.e. which binds specifically with the primary antibody) conjugated to a marker such as a fluorescent label (e.g. fluorescein or rhodamine) or an enzyme (e.g. horseradish peroxidase). Microscopic slides are then assessed for the immune distribution of the protein of interest, and the results are compared with the reporter-specific histochemistry and the level of secreted enzyme activity.

Myocyte Protocols

Primary neonatal cardiac myocyte cultures are used to assess model myocardial formulation parameters and expression conditions for a nucleic acid vector of interest. An established methodology is used to create primary cultures of rat neonatal ventricular myocytes (Parker et al., 1990, J. Clin. Invest. 85:507–514; Thaik et al., 1995, J. Clin. Invest. 96:1093–1099). Sprague-Dawley rats are used at two days of age. Hearts are freshly harvested and cultured as described (Parker et al., 1990, J. Clin. Invest. 85:507–514; Thaik et al., 1995, J. Clin. Invest. 96:1093–1099). Typically after overnight incubation in medium containing 5% (v/v) horse serum, the medium is replaced by serum-free medium. Transfection studies are then performed as described (Parker et al., 1990, J. Clin. Invest. 85:507–514; Thaik et al., 1995. J. Clin. Invest. 96:1093–1099), using methodology comparable to that used for CHO cells, as described herein.

In order to determine any cytotoxic effects that the PLGA or polylysine formulation can have, or to detect another unexpected toxicity, representative cell culture plates are assessed by microscopy to determine the extent of necrotic cell death, as described (Subramanian et al., 1995, Cell Growth Differ. 6: 131–137) and apoptosis. Apoptosis is determined using the terminal transferase-mediated dUTP-biotin nick end-labeling (TUNEL) assay, as described (Kirshenbaum et al., 1996, Dev. Biol. 179:402–411). Initial studies are performed using myocytes involve nanoparticles comprising reporter DNA, and repeat the studies performed using CHO cells, in order to document any difference(s) between the two cell lines.

Once comparable data have been generated, the myocytes are used to study a nucleic acid vector comprising an expression construct encoding the candidate therapeutic gene, HERG (A561V). Because no antibody is available that will distinguish the wild type HERG protein from the HERG (A561V) protein, an epitope (FLAG) tag is incorporated at the amino terminal end of the HERG (A561V) expression construct HERG (A561V) expression is monitored by monitoring the presence of the octapeptide FLAG™ (Eastman Kodak) sequence, as described (Chubet et al., 1996, Biotechniques 20:136–141; Shelness et al., 1994, J. Biol. Chem. 269:9310–9318).

Therapeutic Gene Studies Using a Reverse Gene Therapy Vector

A nucleic acid (e.g. a cDNA) encoding the mutant K channel gene HERG (A561V) is operably linked with the CMV promoter, the α-MyHC promoter, or the ANF promoter to form a HERG (A561V) expression construct. Other potentially cardiac-specific promoters have been described and can optionally be used in the nucleic acid vector described herein. These promoters include cardiac α-actin (Biben et al., 1996, Develop. Biol. 173:200–212) and MCLC2v (Hunter et al., 1995, J. Biol. Chem. 270:173–178). The HERG (A561V) expression construct is incorporated into the pSP64 transcription vector using standard methods. The HERG (A561V) expression construct is also inserted into a pFLAGCMV2 plasmid (Eastman-Kodak), as described (Chubet et al., 1996, Biotechniques 20:136–141; Shelness et al., 1994, J. Biol. Chem. 269:9310–9318). The pFLAGCMV2 plasmid comprises the FLAG sequence, a polylinker region for recombination, and the CMV promoter. Following fusion of the FLAG™ coding sequence and the HERG (A561V) coding sequence, the recombinant protein expressed is tagged with the FLAG™ octapeptide sequence to form a fusion protein.

The FLAG™ octapeptide sequence on the HERG(A561 V)-(FLAG™ octapeptide) fusion protein can be detected using known immunohistochemical methods (Chubet et al., 1996, Biotechniques 20:136–141; Shelness et al., 1994, J. Biol. Chem. 269:9310–931) which involve use of an Anti-FLAG™ Monoclonal Antibody (M5). Thus, the presence of FLAG™ octapeptide indicates expression of HERG (A561V) protein, and this immunohistochemical assay can be used to localize the HERG (A56V) - FLAG fusion protein in order to determine transformation efficiency membrane localization, and tissue distribution of the fusion protein.

Animal Model Experiments

Experiments are performed using dogs as a model of re-entrant atrial flutter in order to determine an optimal method of delivery of nanoparticles to atrial myocardium. The spatial distribution of the nanoparticles within the atrial myocardium and distal cardiac structures is assessed following delivery, using fluorescently-labeled particles. Myocardium and other cardiac tissues transformed using a nucleic acid vector comprising either a reporter construct or the FLAG-HERG conjugate is examined using specific reporter assays or immunolocalization assays in order to determine the distribution and extent of transformation effected using a given vector. Both sectioned samples and tissue planes cut en face are used to perform these assays, using established techniques (e.g. Mondy et al., 1997, Circ. Res. 81:320–327). The effect of delivery of nanoparticles comprising an expression construct encoding the HERG (A561V) protein upon induction of atrial flutter and related ventricular and atrial electrophysiologic parameters is assessed.

Short Term (72 hour) Dog Experiments

The goals of these acute dog studies are to investigate DNA-containing nanoparticle delivery techniques and early events involved in the mechanisms of the distribution of nanoparticle-mediated transfection in the canine myocardium. These 72 hour studies are used to determine optimal nucleic acid vector delivery conditions, the acute distribution of nanoparticles in the re-entry circuit, and the extent of any acute cardiac or systemic spread of the nucleic acid vector. These studies are also used to determine whether local delivery of DNA-containing nanoparticles affects inducibility of atrial flutter or other electrophysiologic parameters. Using the Frame Y-incision model, a DNA-containing nanoparticle suspension is injected using a 27 gauge needle into the atrial myocardium of each dog, just below the subtransverse incision site. This juncture of the reentry loop is critical, and conduction block in this region should limit or prevent inducibility of atrial flutter.

Non-recovery studies initially involve use of fluorescently labeled nanoparticles 500 nanometers in diameter Ultra-brite™ (Polysciences, Warrington, Pa.). Histology studies are performed to determine the distribution of fluorescently labeled nanoparticles at the site of administration and adjacent myocardial regions. Once ideal nanoparticle concentration and delivery conditions have been established, a series of 72 hour studies are performed using nanoparticles comprising a reporter construct in order to determine expression of the reporter construct in the atrial myocardium, expression at remote cardiac sites, and acute bioavailability in the atrial myocardium using PCR analyses with appropriate primers. Local and distal myocardium, liver, lung, kidney, and gonads are sampled for these assays.

Chronic Dog Studies

The goals of these chronic dog studies are to examine expression and effects on atrial flutter effected by administration of nanoparticle formulations that are judged to be optimal in cell culture studies and acute dog studies. Initial experiments focus on reporter studies to determine the extent of expression, examining both the percentage of nuclei in the region of interest which express the β-galactosidase reporter protein. The initial experiments also indicate the effect(s) of nanoparticle delivery on preventing atrial flutter and related electrophysiologic parameters. Effects of nanoparticle delivery on distal cardiac sites, as well as distal organs, are examined both for reporter protein expression and for the presence of nucleic acid vector, as determined by PCR.

Transformation of atrial myocardium using nanoparticles comprising an expression construct encoding HERG (A561V) protein operably linked with a CMV promoter or a cardiac tissue specific promoter is though to cause conduction block and thereby inhibit atrial flutter. This is confirmed using the methods described herein. The tricuspid annulus from each chronic dog is explanted at the time of sacrifice (i.e. 4 weeks post-surgery) and examined to determine precise regional differences in cardiac conduction parameters in the reentry circuit, as described (Fei et al., 1997, Circ. Res. 80:242–252). Transformation effected using nucleic acid vector-containing nanoparticles is compared with transformation effected by injection of the nucleic acid vector alone (i.e. not contained in or on a nanoparticle).

Animal Model Procedure: "Y"-Shaped Lesion/Atriotomy Studies

Atrial flutter is induced in dogs using a modification of published procedures (Frame, 1986, Circ. Res. 58:495–511; Buchanan et al., 1993, J. Cardiovasc. Pharmacol. 33:10–14). Male mongrel dogs weighing 25 to 35 kilograms are used in these model studies. General anesthesia using sodium pentobarbital is followed by a right thoracotomy. A "Y"-shaped lesion right atrial incision is at the inferior board of the atrium along the inferior vena cava as described (Frame, 1986. Circ. Res. 58:495–511; Frame et al., 1987, Circulation 5:1155–1175; Boyden et al., 1989, Circulation 79:406–416). The strategy of this approach is to create a permanent conduction block in the right atrium that results in a re-entry loop for atrial impulse conduction for inducing atrial flutter. The "Y"-shaped lesion is closed using 4–0 silk with a continuous interlocking suture, the spacing between each visible suture not to exceed 5 millimeters. Burst pacing episodes can be used to create a reproducible re-entrant circuit involving a pathway around the tricuspid annulus. This model, which induces physiological responses which closely parallel those observed for atrial flutter in humans (Frame, 1996, Cardiol. Clin. 14:471–481), allows atrial flutter to be induced in both an acute and chronic animal study setting. Atrial flutter in this model can also be stopped and re-induced using appropriate pacing protocols as described (Frame et al., 1986, Circ. Res. 58:495–511; Frame et al., 1987, Circulation 5:1155–1175; Boyden et al., 1989. Circulation 79:406–416).

Atrial Flutter Induction

Each experimental atrial flutter induction study comprises eight or more attempts to inducing atrial flutter using burst pacing at 3 milliamp or greater (double capture threshold) for 3 seconds at cycle lengths of 150 milliseconds, 140 milliseconds, 130 milliseconds, 120 milliseconds, 110 milliseconds, and 100 milliseconds. Atrial flutter that continues for five minutes or more is defined as persistent flutter, indicating successful induction. The frequency of inducibility with respect to the number of sustained episodes or attempts to induce atrial flutter before and after placement of a nucleic acid vector delivery system, or a non-DNA-containing implant, is used as a basis for measuring drug effects. Atrial flutter episodes are terminated after five minutes by overdrive pacing as described (Labhasetwar et al., 1994, J. Cardiovasc. Pharm. 24:826–840; Frame et al., 1986, Circ. Res. 58:495–511: Frame et al., 1987. Circulation 5:1155–1175; Boyden et al., 1989, Circulation 79:406–416), or if necessary, by counter-shock. Animals are allowed at least 5 minutes between induction to be certain of rhythm and blood pressure stability. Animals which are not inducible for sustained flutter are excluded from these studies.

Arrhythmia and Electrophysiolopic Endpoints

Animals investigated in this model, both in acute and chronic studies are assessed from the point of view of a number of parameters affecting atrial arrhythmias. These include the following:

Atrial flutter induction: the frequency of successful inductions before and after nanoparticle delivery.

Atrial impulse conduction, as assessed by multi-electrode studies, as described herein.

Electrophysiologic parameters: atrial and ventricular effective refractory periods, sinus node recovery time, atrial flutter cycle length, ventricular rate response, conduction time, and AV-node conduction time.

Epicardial Mapping and Related Electrophysiologic Assessment

Figure 8:
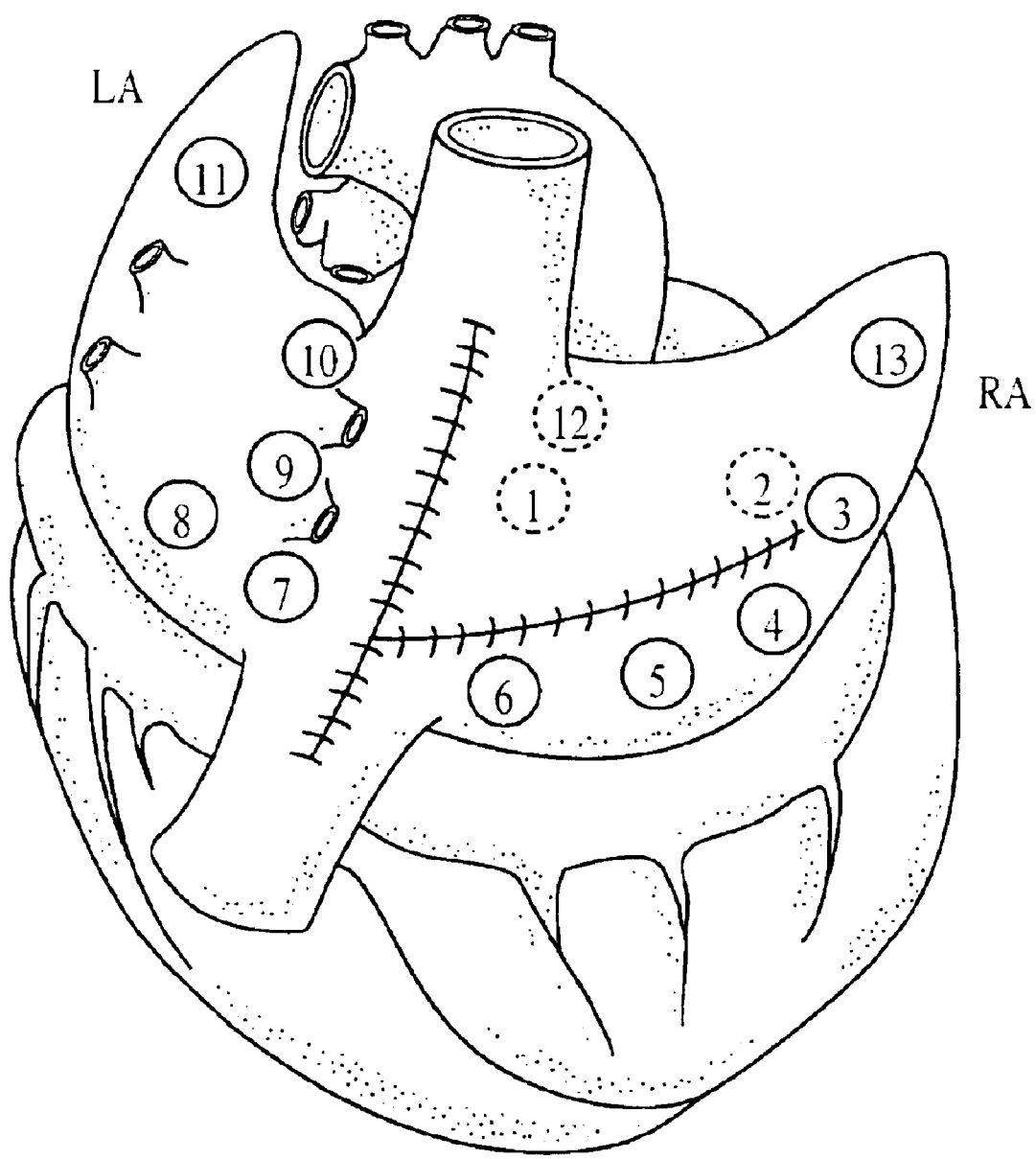
FIG. 8 is a diagram which depicts placement of epicardial electrodes in a dog, as described herein.

The non-recovery procedures and the terminal procedure in chronic dogs characterize the sequence of activation of the reentry loop in the "Y"-shaped lesion model. The technique for epicardial mapping utilizes a published methodology (Frame. 1986, Circ. Res. 58:495–511). FIG. 8 illustrates the placement of epicardial electrodes. Electrodes #1 through #6 in FIG. 8 and a right atrial appendage recording site (Site # 13 in FIG. 8) are used. Bipolar platinum epicardial electrodes are used, and are connected with a CODAS analog-to-digital conversion system and computer. The types of measurements of greatest interest are the sequence of activation times for impulse spread beginning from the first electrode site as illustrated in FIG. 8, with respect to changes due to implantation of a controlled release drug delivery system.

The general protocol to be used in these epicardial mapping studies and investigations of the reentry mechanism involves the following. Inducibility is determined, in terms of whether animals develop atrial flutter following the creation of a "Y"-shaped lesion. Next, epicardial electrodes are placed as illustrated in FIG. 8 and described herein. The sequence of epicardial activation is determined and recorded. Epicardial ventricular electrodes are implanted, and the animals are outfitted with a transvenous monophasic action potential electrode catheter. Pacing is carried out with a separate right atrial pacing electrode in acute (non-recovery) studies. Electrophysiologic measurements of interest include comparisons made during pacing of the atrial effective refractory period before and after drug system placement, ventricular effective refractory period, changes in cycle length, and atrial flutter cycle length. The monophasic action potential duration in the right atrium, and in the right ventricle is also determined during pacing. All of these measurements, and sequence of activation studies are performed before and after acute drug administration. More extensive atrial mapping can be performed if the electrophysiologic and atrial flutter data indicate this to be necessary or desirable.

Figure 9:
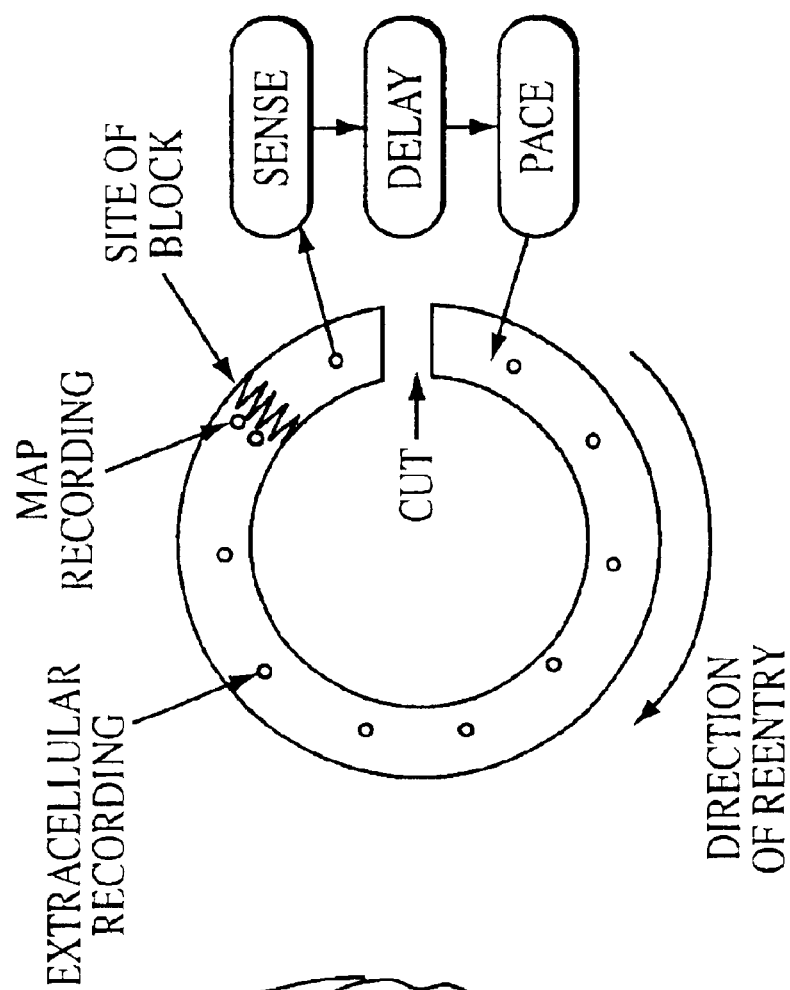
FIG. 9 is a diagram which depicts placement of electrodes in the vicinity of the tricuspid annulus of a dog, as described herein.
Figure 9:
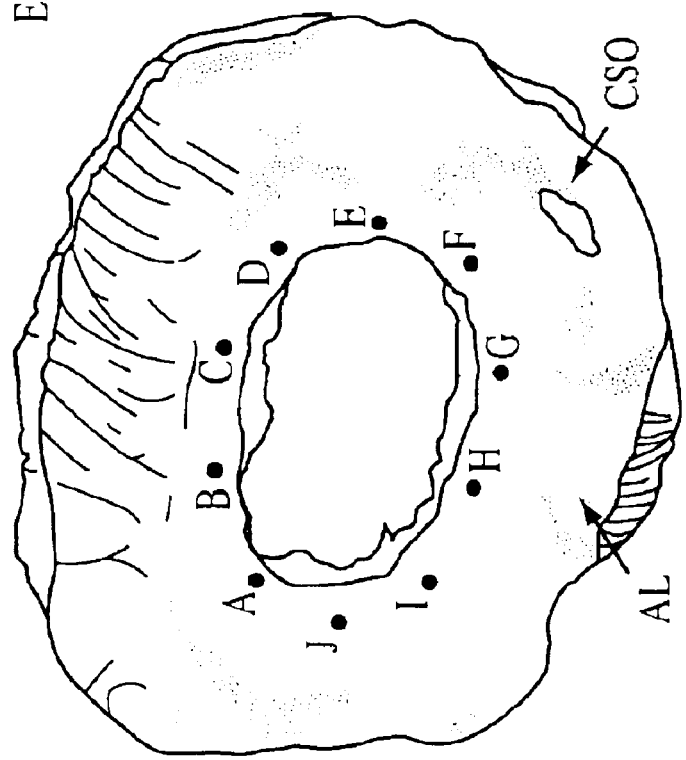

All chronic studies, at their termination, involve explantation of the tricuspid ring, and in vitro studies are performed. Typical preparations involve rapidly excising the heart at the time of euthanasia, and dissecting it in cold Tyrode's solution, equilibrated with 95% oxygen and 5% $CO_2$. The tricuspid ring is dissected and mounted with the endocardium upward in a tissue bath. The tricuspid annulus is instrumented using electrodes, as illustrated in FIG. 9, focusing on the area of nucleic acid vector delivery or control nanoparticle injection. The goal of these studies is to investigate regional differences in conduction attributable to expression of either reporter constructs or expression constructs, such as an expression construct encoding HERG (A561V) protein. Following the end of the electrophysiologic study period, morphology sampling is performed, and the orientation of samples for microscopic investigation is noted with respect to the site of nanoparticle delivery, the site of expression of the nucleic acid vector, the location of electrophysiologic recording regions, and the proximity to the transverse incision and the remainder of the reentry circuit.

Morphologic techniques are used to image reporter expression, both with X-gal staining, and immunohistochemistry to detect β-galactosidase activity. In animals transformed with HERG (A561V), immunohistochemical studies are performed using a commercially available monoclonal antibody to the FLAG™ octapeptide fused with HERG (A561V). Routine hematoxylin- and eosin-stained microscopy are performed for morphologic assessment of any cellular response to nanoparticle administration or toxicity related to the polylysine conjugates.

The disclosures of each and every patent, patent application, and publication cited herein are hereby incorporated herein by reference in their entirety.

While this invention has been disclosed with reference to specific embodiments, it is apparent that other embodiments and variations of this invention can be devised by others skilled in the art without departing from the true spirit and scope of the invention. The appended claims are intended to be construed to include all such embodiments and equivalent variations.

What is claimed is:

1. A method of alleviating reentry atrial flutter in an affected animal cell, said method comprising locally delivering to a cardiac cell a reverse gene therapy vector comprising a promoter operably linked with a nucleic acid encoding a therapeutic gene product which is usually only expressed in cells of an abnormal tissue that is not afflicted with reentry atrial flutter, wherein said therapeutic gene product is a defective HERG protein, and delivery of said vector to the affected cardiac cell alleviates the flutter.

2. The method of claim 1, wherein the defective HERG protein is selected from the group consisting of HERG (A561V) protein and MIRP protein.

3. The method of claim 1, wherein the promoter is a cardiac tissue specific promoter.

4. The method of claim 3, wherein the cardiac tissue-specific promoter is selected from the group consisting of the ANF promoter and the α-MyHC promoter.

5. The method of claims 1, wherein the cell is a myocardial cell.

6. The method of claim 5, wherein the cell is a right atrial myocardium cell.

7. The method of claim 5, wherein the cell is a cell of the crista terminalis.

8. The method of claim 5, wherein the defective HERG protein is HERG (A561 V) protein.

9. The method of claim 8, wherein the promoter is a cardiac tissue-specific promoter.

10. The method of claim 9, wherein the cardiac tissue-specific promoter is selected from the group consisting of the ANF promoter and the α-MyHC promoter.

11. The method of claim 2, wherein the defective HERG protein is MIRP protein.

12. The method of claim 11, wherein the promoter is cardiac tissue-specific promoter.

13. The method of claim 12, wherein the cardiac tissue-specific promoter is selected from the group consisting of the ANF promoter and the α-MyHC promoter.

* * * * *